(12) United States Patent
Botas et al.

(10) Patent No.: US 7,847,146 B2
(45) Date of Patent: Dec. 7, 2010

(54) MODEL FOR NEURODEGENERATIVE DISORDERS

(75) Inventors: Juan Botas, Houston, TX (US); Diego Rincon-Limas, Galveston, TX (US); Pedro Fernandez-Funez, Galveston, TX (US); Ismael Al-Ramahi, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 10/852,950

(22) Filed: May 25, 2004

(65) Prior Publication Data

US 2005/0114912 A1      May 26, 2005

Related U.S. Application Data

(63) Continuation-in-part of application No. 10/402,420, filed on Mar. 28, 2003, now abandoned.

(51) Int. Cl.
*G01N 33/00* (2006.01)
*A01K 67/00* (2006.01)

(52) U.S. Cl. ............... 800/3; 800/8; 800/9; 800/12; 800/13

(58) Field of Classification Search .............. 800/3, 800/9, 12
See application file for complete search history.

(56) References Cited

U.S. PATENT DOCUMENTS

2002/0174446 A1    11/2002   Cohen et al.

FOREIGN PATENT DOCUMENTS

| WO | WO0112238 A1 | 2/2001 |
| WO | WO0226820 | 4/2002 |

OTHER PUBLICATIONS

1999, Crabbe et al., Science, vol. 284, pp. 1670-1672.*
Cao et al., 2008, Genetics, vol. 178, pp. 1457-1471.*
Whittman et al., 2001, Science, vol. 293, pp. 711-714.*
Rockenstein et al., 2007, Adv. Drug Delivery Rev., vol. 59, pp. 1093-1102.*
Spradling AC, Gene diruptions in P transosable elements: an integral component of the Drosophila genome project, 1995, 92, pp. 10824-10830.*
Atkinson PW, Genetic transformation systems in insects, 2001, Annu. Rev. Entomol., vol. 46, pp. 317-346.*
Lewis J, Enhanced neurofibrillary degeneration in transgenic mice expressing mutant tau and APP, 2001, Science, vol. 293, pp. 1487-1491.*
Fossgreen A, Transgenic Drosophila expressing human amyloid precursor protein show gamma-secretase activity and a blistered-wing phenotype, 1998, PNAS, vol. 95 pp. 13703-13708.*
O'Brochta DA, Gene vector and transposable element behavior in mosqitoes, 2003, J. Experimental Biology, vol. 206, pp. 3823-3834.*
Nitasaka E, Repressor of P elements in Drosophila melanogaster: cytotype determination by a defective P element carrying only open reading frames 0 through 2, 1987, PNAS, vol. 84, pp. 7605-7608.*
Luo, L., Human Amyloid Precursor Protein Ameliorates Behavioral Deficit of Flies Deleted for APPL Gene. Neuron, Oct. 1992, vol. 9, pp. 595-605.
Torroja, L., Neuronal Expression of APPL, the Drosophila Homologue of the Amyloid Precursor Protein (APP), Disrupts Axonal Transport. Current Biology, Apr. 1999, vol. 9, pp. 489-492.
Himmler, A., Tau Consists of a Set of Proteins with Repeated C-terminal Microtubule-Binding Domains and Variable N-terminal Domains. Molecular and Cellular Biology. Apr. 1989, vol. 9, pp. 1381-1388.
Freeman, M., The Argos Gene Encodes a Diffusible Factor that Regulates Cell Fate Decisions in the Drosophila Eye. Cell. Jun. 1992, vol. 69, pp. 963-975.
Jackson, G.R., Human Wild-type Tau Interacts with Wingles Pathway Components and Produces Neurofibrillary Pathology in Drosophila. Neuron. May 2002, vol. 34, pp. 509-519.
Gotz et al., "Formation of Neurofibrillary Tangles in P301L Tau Transgenic Mice Induced by Aβ42 Fibrils," Science (2001) 293:1491-1495.
Supplementary European Search Report for corresponding European Appl. No. 04759683.8, issued Jun. 25, 2008.
Jackson, G.R., et al 91998). Neuron 21: 633-642.
Kazemi-Esfarani, P. and Brenzer, S. (2000). Science 287: 1837-1840.
Feany, M.B. and Bender, W. W. (2000). Nature 404: 394-398.
Rosen et al., Proc. Natl. Acad. Sci. U.S.A. 86:2478-2482 (1988).
Luo, et al., Neuron 9:595-605 (1992).
Fernandez-Funez, et al. (2000) Nature 408 (6808): 101-6.

\* cited by examiner

*Primary Examiner*—Peter Paras, Jr.
*Assistant Examiner*—David Montanari
(74) *Attorney, Agent, or Firm*—Edwards Angell Palmer & Dodge LLP; Elizabeth Spar; Kathleen Williams

(57) ABSTRACT

The present invention discloses a double transgenic fly that expresses both Tau protein and the human Aβ42 peptide of human amyloid-β precursor protein (APP). The double transgenic flies of the present invention display a synergistic altered phenotype as compared to the altered phenotype displayed by transgenic flies expressing either Tau or human Aβ42 alone, and thus provide for an improved model for neurodegenerative disorders, such as Alzheimer's disease. The invention further discloses methods for identifying for therapeutic compounds to treat neurodegenerative disorders using the double transgenic flies.

24 Claims, 10 Drawing Sheets

FIGURE 1A

Aβ42 Amino acid sequence
DAEFRHDSGYEVHHQKLVFFAEDVGSNKGAIIGLMVGGVVIA
(SEQ ID NO:1)

FIGURE 1B

Aβ42 Nucleic acid sequence
gatgcagaattccgacatgactcaggatatgaagttcatcatcaaaaattggtgttctttgcagaagatgtgg
gttcaaacaaaggtgcaatcattggactcatggtgggcggtgttgtcatagcgtga (SEQ ID NO:2)

FIGURE 2A

MAEPRQEFEVMEDHAGTYGLGDRKDQGGYTMHQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQARMVSKSKDGTGSDDKKAKGADGKTK

IATPRGAAPPGQKGQANATRIPAKTPPAPKTPPSSGEPPKSGDRSGYSSP

GSPGTPGSRSRTPSLPTPPTREPKKVAVVRTPPKSPSSAKSRLQTAPVPM

PDLKNVKSKIGSTENLKHQPGGGKVQIINKKLDLSNVQSKCGSKDNIKHV

PGGGSVQIVYKPVDLSKVTSKCGSLGNIHHKPGGGQVEVKSEKLDFKDRV

QSKIGSLDNITHVPGGGNKKIETHKLTFRENAKAKTDHGAEIVYKSPVVS

GDTSPRHLSNVSSTGSIDMVDSPQLATLADEVSASLAKQGL (SEQ ID NO: 3)

FIGURE 2B atggctgagccccgccaggagttcgaagtgatggaagatcACGCTGGGAC
GTACGGGTTGGGGGACAGGAAAGATCAGGGGGGCTACACCATGCACCAAG
ACCAAGAGGGTGACACGGACGCTGGCCTGAAAGAATCTCCCCTGCAGACC
CCCACTGAGGACGGATCTGAGGAACCGGGCTCTGAAACCTCTGATGCTAA
GAGCACTCCAACAGCGGAAGATGTGACAGCACCCTTAGTGGATGAGGGAG
CTCCCGGCAAGCAGGCTGCCGCGCAGCCCCACACGGAGATCCCAGAAGGA
ACCACAGCTGAAGAAGCAGGCATTGGAGACACCCCAGCCTGGAAGACGA
AGCTGCTGGTCACGTGACCCAAGCTCGCATGGTCAGTAAAAGCAAAGACG
GGACTGGAAGCGATGACAAAAAAGCCAAGGGGGCTGATGGTAAAACGAAG
ATCGCCACACCGCGGGGAGCAGCCCTCCAGGCCAGAAGGGCCAGGCCAA
CGCCACCAGGATTCCAGCAAAAACCCCGCCCGCTCCAAAGACACCACCCA
GCTCTGGTGAACCTCCAAAATCAGGGGATCGCAGCGGCTACAGCAGCCCC
GGCTCCCCAGGCACTCCCGGCAGCCGCTCCCGCACCCCGTCCCTTCCAAC
CCCACCCACCCGGGAGCCCAAGAAGGTGGCAGTGGTCCGTACTCCACCCA
AGTCGCCGTCTTCCGCCAAGAGCCGCCTGCAGACAGCCCCCGTGCCCATG
CCAGACCTGAAGAATGTCAAGTCCAAGATCGGCTCCACTGAGAACCTGAA
GCACCAGCCGGGAGGCGGGAAGGTGCAGATAATTAATAAGAAGCTGGATC
TTAGCAACGTCCAGTCCAAGTGTGGCTCAAAGGATAATATCAAACACGTC
CCGGGAGGCGGCAGTGTGCAAATAGTCTACAAACCAGTTGACCTGAGCAA
GGTGACCTCCAAGTGTGGCTCATTAGGCAACATCCATCATAAACCAGGAG
GTGGCCAGGTGGAAGTAAAATCTGAGAAGCTTGACTTCAAGGACAGAGTC
CAGTCGAAGATTGGGTCCTGGACAATATCACCCACGTCCCTGGCGGAGG
AAATAAAAAGATTGAAACCCACAAGCTGACCTTCCGCGAGAACGCCAAAG
CCAAGACAGACCACGGGGCGGAGATCGTGTACAAGTCGCCAGTGGTGTCT
GGGGACACGTCTCCACGGCATCTCAGCAATGTCTCCTCCACCGGCAGCAT
CGACATGGTAGACTCGCCCCAGCTCGCCACGCTAGCTGACGAGGTGTCTG
CCTCCCTGGCCAAGCAGGGTTTGTGATCAGGCCCCTGGGGCGGTCAATAA
TTGTGGAGAGGAGAGAATGAGAGAGTGTGGAAAAAAAAGAATAATGACC
CGGCCCCCGCCCTCTGCCCCC (SEQ ID NO: 4)

FIGURE 3

| TAU MUTATIONS | REFERENCES |
|---|---|
| P301L | Hutton, M. et al., Nature 393: 702-708 (1998) |
| G272V | Hutton, M. et al., Nature 393: 702-708 (1998) |
| R406W | Tatebayashi, Y. et al., Proc. Nat. Acad. Sci. 99: 13896-13901 (2002) |
| V337M | Hutton, M. et al., Nature 393: 702-705 (1998) |
| N279K | Clark, L. et al., Proc. Nat. Acad. Sci. 95: 13103-13107 (1998) |
| G389R | Murrell, J.R. et al., J. Neuropath. Exp. Neurol. 58: 1207-1226 (1999) |
| P301S | Yasuda, M. et al., Neurology 55: 1224-1227 (2000) |
| N296N | Spillantini, M.G. et al. Ann. Neurol. 48: 939-943 (2000) |
| E342V | Lippa, C.F. et al., Ann. Neurol. 48: 850-858 (2000) |
| K257T | Pickering-Brown, S. et al., Ann. Neurol. 48: 859-867 (2000) |
| K339I | Neumann, M., Ann. Neurol. 50: 503-513 (2001) |
| S305N | Iijima, M. et al., Nueroreport 10: 497-501, (1999) |
| R5H | Hayashi, S. et al., Ann Neurol. 51: 525-530 (2002) |
| S320F | S.M. van Herpen, et al., Ann Nuerol. 51: 373-376 (2002) |
| R5L | Poorkaj, P. et al, Ann Nuerol. 52: 511-516 (2002) |

FIGURE 4

Signal Peptide Sequences

Dint (*wingless*) Signal peptide Amino acid sequence

MDISYIFVICLMALSGGS (SEQ ID NO: 5)

Dint (*wingless*) Signal peptide plus linker Nucleic acid sequence atggatatcagctatatcttcgtcatctgcctgatggccctgtgcagcgg cggcagcagcttcgcgatg (SEQ ID NO: 6)

Argos Signal Peptide Amino acid sequence

*MPTTLMLLPCMLLLLLTAAAVAVGG* (SEQ ID NO: 7)

Argos Signal Peptide Nucleic acid sequence atgcctacgacattgatgttgctgccgtgcatgctgctgttgctgctgac cgccgctgccgttgctgtcggcggc (SEQ ID NO: 8)

US 7,847,146 B2

MODEL FOR NEURODEGENERATIVE DISORDERS

RELATED APPLICATIONS

This application is a continuation-in-part of application Ser. No. 10/402,420, filed Mar. 28, 2003 now abandoned. The entire teachings of the above application are incorporated herein by reference.

GOVERNMENT SUPPORT

The invention was supported, in whole or in part, by a grant number NS42179 from the National Institute of Health The Government has certain rights in the invention.

BACKGROUND

Alzheimer's disease (AD) is the most common neurodegenerative disorder in humans. The disease is characterized by a progressive impairment in cognition and memory. The hallmark of AD at the neuropathological level is the extracellular accumulation of the amyloid-β peptide (Aβ) in "senile" plaques, and the intracellular deposition of neurofibrillary tangles made of the microtubule-associated protein Tau. In neuronal tissue of AD patients, Tau is hyperphosphorylated and adopts pathological conformations evident with conformation-dependent antibodies. The amyloid-β peptide is a cleavage product of the amyloid precursor protein (APP). In normal individuals, most of Aβ is in a 40-amino acid form, but there are also minor amounts of Aβ that are 42 amino acids in length (Aβ42). In patients with AD, there is an overabundance of Aβ42 that is thought to be the main toxic Aβ form.

A number of transgenic mouse models have been generated that express wild-type or mutant human APP. The mutant form of APP is differentially cleaved to result in increased amounts of Aβ42 deposited within Aβ plaques. These transgenic mice present with neurological symptoms of Alzheimer's disease, such as impaired memory and motor function (Janus C. et al., Curr. Neurol. Neurosci. Rep 1 (5): 451-457 (2001)). A transgenic mouse that expresses both mutant human APP and mutant human Tau has also been generated (Jada, et. al., Science, (5534) 293:1487-1491 (2001)). This double transgenic mouse is a rodent model for AD that shows enhanced neurofibrillary degeneration indicating that either APP or Aβ influences the formation of neurofibrillary tangles.

Mouse models have proven very useful for testing potential AD therapeutics. However, the use of mice for testing therapeutics is both expensive and time consuming. Thus, it would be beneficial to find alternative models which are less expensive and that can be efficiently used to screen for therapeutic agents for Alzheimer's disease. For example, non-mammalian animal models, such as *Caenorhabditis elegans* or *Drosophila melanogaster*.

Although human amyloid precursor protein (APP) has been expressed in *Drosophila melanogaster* (Fossgreen, et. al., PNAS 95:13703-13708 (1998); Yagi et al., Mol. Cell. Biol. Res. Comm. 4: 43-49 (2000)), the expression of human APP in *Drosophila* has proven unsuccessful for generating disease models with Aβ42 plaque depositions. Cohen et. al. (U.S. Pat. Appl. Pat. No. 2002/0174446) discloses a transgenic *Drosophila* carrying a cDNA encoding Aβ42 peptide fused to a signal peptide. Expression of Aβ42 in the *Drosophila* eye of this model reportedly exhibits a rough-eye phenotype. However, expression levels of Aβ42 peptide are variable, and only high levels of Aβ42 peptide results in the rough-eye phenotype of the fly. Transgenic *Drosophila* overexpressing wild-type and mutant forms of human Tau also have been generated (Wittman et al., Science 293:711-714 (2001); Jackson et al., Neuron 34: 509-519 (2002)). In flies, expression of human Tau can lead to shortened life-span, loss of cholinergic neurons (Wittman et al., Science 293:711-714 (2001)) and eye phenotypes (Jackson et al., Neuron 34: 309-519 (2002)). However, these wild type and mutant transgenic Tau fly models do not develop, on their own, neurofibrillary tangles characteristic of human AD. Neurofibrillary pathology was only observed when combined with other alterations in genes of the Wint signaling pathway (Jackson et al., Neuron 34: 309-519 (2002)).

Thus, despite significant advances in the field, there is still a need in the art for improved non-mammalian animal models of Alzheimer's disease that can be easily and inexpensively generated for screening potential therapeutic agents.

SUMMARY OF THE INVENTION

The present invention discloses a double transgenic fly that expresses both the Tau protein and the human Aβ42 peptide of APP. The double transgenic flies of the present invention display a synergistic altered phenotype as compared to the altered phenotype displayed by transgenic flies expressing either Tau or human Aβ42 alone. Thus, the flies provide for models of neurodegenerative disorders, such as Alzheimer's disease. Accordingly, the invention further discloses methods for identifying therapeutic compounds useful for treating neurodegenerative disorders, such as Alzheimer's disease.

The present invention provides a transgenic fly whose somatic and germ cells comprise two transgenes operatively linked to a promoter, wherein the transgenes encode Tau and human Aβ42, and wherein the expression of the transgenes in the nervous system results in the fly having a predisposition to, or resulting in, progressive neural degeneration.

In one embodiment, the transgenic fly is transgenic *Drosophila*.

In preferred embodiments of the invention, the Tau and human Aβ42 transgenes are operatively linked to an expression control sequence and expression of the transgenes results in an observable phenotype. In one embodiment, the transgene is temporally regulated by the expression control sequence. In another embodiment, the transgene is spatially regulated by the expression control sequence. In a specific embodiment of the invention, the expression control sequence is a heat shock promoter. In a preferred mode of the embodiment, the heat shock promoter is derived from the hsp70 or hsp83 genes. In other specific embodiments, the Tau and human Aβ42 transgenes are operatively linked to a Gal4 Upstream Activating Sequence ("UAS"). Optionally, the transgenic *Drosophila* comprising Tau and human Aβ42 transgenes further comprise a GAL4 gene. In a preferred embodiment, the GAL4 gene is linked to a tissue specific expression control sequence. In a preferred mode of the embodiment, the tissue specific expression control sequence is derived from the sevenless, eyeless, gmr/glass or any of the rhodopsin genes. In another preferred mode of the embodiment, the tissue specific expression control sequence is derived from the dpp, vestigial, or apterous genes. In another preferred mode of the embodiment, the tissue specific expression control sequence is derived from neural-specific genes like elav, nirvana or D42 genes. In yet other embodiments, the expression control sequence is derived from ubiquitously expressed genes like tubulin, actin, or ubiquitin. In yet other embodiments, the expression control sequence comprises a tetracycline-controlled transcriptional activator (tTA)

responsive regulatory element. Optionally, the transgenic *Drosophila* comprising the Tau and human Aβ42 transgenes further comprise a tTA gene.

In one embodiment, the transgenic fly comprises Aβ42 and Tau DNA sequences represented by SEQ ID NO: 2 and SEQ ID NO: 4, respectively.

The DNA sequence encoding human amyloid-β peptide Aβ42 may be fused to a signal peptide, e.g., via an amino acid linker. The signal peptide may be a wingless (wg) signal peptide, such as the peptide represented by SEQ ID NO: 5, or an Argos (aos) signal peptide, such as the sequence of SEQ ID NO: 7. The transgenic fly may exhibit an altered phenotype, such as a rough eye phenotype, a concave wing phenotype, a locomotor dysfunction (e.g., reduced climbing ability, reduced walking ability, reduced flying ability, decreased speed, abnormal trajectories, and abnormal turnings), abnormal grooming, other abnormal behaviors, or reduced life span.

In another aspect, the invention relates to a method for identifying an agent active in neurodegenerative disease. The method comprises the steps of: (a) providing a transgenic fly whose genome comprises DNA sequences that encode human amyloid-β peptide Aβ42 and Tau protein; (b) providing a candidate agent to the transgenic fly; and (c) observing the phenotype of the transgenic fly of step (b) relative to the control fly that has not been administered an agent. An observable difference in the phenotype of the transgenic fly that has been administered an agent compared to the control fly that has not been administered an agent is indicative of an agent active in neurodegenerative disease. In yet another aspect, the invention relates to a method for identifying an agent active in neurodegenerative disease. The method comprises the steps of: (a) providing a transgenic fly and a control wild-type fly; (b) providing a candidate agent to the transgenic fly and to the control fly; and (c) observing a difference in phenotype between the transgenic fly and the control fly, wherein a difference in phenotype is indicative of an agent active in neurodegenerative disease.

BRIEF DESCRIPTION OF FIGURES

FIG. 1a shows an amino acid sequence of Aβ42 (SEQ ID NO: 1).

FIG. 1b shows a nucleotide sequence of Aβ42 (SEQ ID NO: 2).

FIG. 2a shows an amino acid sequence of Tau (SEQ ID NO: 3).

FIG. 2b shows a nucleotide sequence Tau (SEQ ID NO: 4).

FIG. 3 shows a list of known Tau mutations.

FIG. 4 shows the amino acid sequence (SEQ ID NO: 5) and nucleotide sequence (SEQ ID NO: 6) of Dint (wingless) signal peptide as well as the amino acid sequence (SEQ ID NO: 7) and nucleotide sequence (SEQ ID NO: 8) of Argos (aos) signal peptide.

DETAILED DESCRIPTION

Figure 5A:
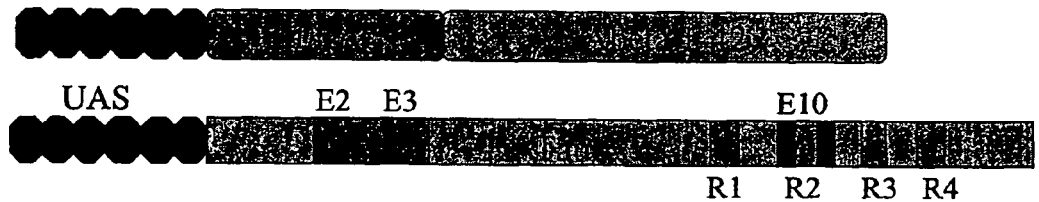
FIG. 5a shows a schematic representation of Aβ42 and Tau constructs.

The present invention discloses a double transgenic fly that expresses both Tau protein and human Aβ42. The Aβ42/Tau double transgenic flies exhibit progressive neurodegeneration which can lead to a variety of altered phenotypes including locomotor phenotypes, behavioral phenotypes (e.g., appetite, mating behavior, and/or life span), and morphological phenotypes (e.g., shape, size, or location of a cell, organ, or appendage; or size, shape, or growth rate of the fly).

As used herein, the term "transgenic fly" refers to a fly whose somatic and germ cells comprise a transgene operatively linked to a promoter, wherein the transgene encodes Tau or human Aβ42, and wherein the expression of said transgenes in the nervous system results in said *Drosophila* having a predisposition to, or resulting in, progressive neural degeneration. The term "double transgenic fly" refers to a transgenic fly comprising foreign genetic material from at least two separate sources, such as the Aβ42/Tau double transgenic fly exemplified herein. Although the exemplified double transgenic fly was produced by crossing two single transgenic flies, the double transgenic fly of the present invention can be produced using any method known in the art for introducing foreign DNA into an animal. The terms "transgenic fly" and "double transgenic fly" include all developmental stages of the fly, i.e., embryonic, larval, pupal, and adult stages. The development of *Drosophila* is temperature dependent. The *Drosophila* egg is about half a millimeter long. It takes about one day after fertilization for the embryo to develop and hatch into a worm-like larva. The larva eats and grows continuously, molting one day, two days, and four days after hatching (first, second and third instars). After two days as a third instar larva, it molts one more time to form an immobile pupa. Over the next four days, the body is completely remodeled to give the adult winged form, which then hatches from the pupal case and is fertile after another day (timing of development is for 25° C.; at 18°, development takes twice as long).

As used herein, "fly" refers to an insect with wings, such as *Drosophila*. As used herein, the term "*Drosophila*" refers to any member of the Drosophilidae family, which include without limitation, *Drosophila funebris, Drosophila multispina, Drosophila subfunebris, guttifera* species group, *Drosophila guttifera, Drosophila albomicans, Drosophila annulipes, Drosophila curviceps, Drosophila formosana, Drosophila hypocausta, Drosophila immigrans, Drosophila keplauana, Drosophila kohkoa, Drosophila nasuta, Drosophila neohypocausta, Drosophila niveifrons, Drosophila pallidifions, Drosophila pulaua, Drosophila quadrilineata, Drosophila siamana, Drosophila sulfurigaster albostrigata, Drosophila sulfurigaster bilimbata, Drosophila sulfurigaster neonasuta, Drosophila Taxon F, Drosophila Taxon I, Drosophila ustulata, Drosophila melanica, Drosophila paramelanica, Drosophila tsigana, Drosophila daruma, Drosophila polychaeta, quinaria* species group, *Drosophila falleni, Drosophila nigromaculata, Drosophila palustris, Drosophila phalerata, Drosophila subpalustris, Drosophila eohydei, Drosophila hydei, Drosophila lacertosa, Drosophila robusta, Drosophila sordidula, Drosophila repletoides, Drosophila kanekoi, Drosophila virilis, Drosophila maculinatata, Drosophila ponera, Drosophila ananassae, Drosophila atripex, Drosophila bipectinata, Drosophila ercepeae, Drosophila malerkotliana malerkotliana, Drosophila* malerkotliana pallens, Drosophila parabipectinata, Drosophila pseudoananassae pseudoananassae, Drosophila pseudoananassae nigrens, Drosophila varians, Drosophila elegans, Drosophila gunungcola, Drosophila eugracilis, Drosophila ficusphila, Drosophila erecta, Drosophila mauritiana, Drosophila melanogaster, Drosophila orena, Drosophila sechellia, Drosophila simulans, Drosophila teissieri, Drosophila yakuba, Drosophila auraria, Drosophila baimaii, Drosophila barbarae, Drosophila biauraria, Drosophila birchii, Drosophila bocki, Drosophila bocqueti, Drosophila burlai, Drosophila constricta (sensu Chen & Okada), Drosophila jambulina, Drosophila khaoyana, Drosophila kikkawai, Drosophila lacteicornis, Drosophila leontia, Drosophila lini, Drosophila mayri, Drosophila parvula, Drosophila pectinifera, Drosophila punjabiensis, Drosophila quadraria, Drosophila rufa, Drosophila seguyi, Drosophila serrata, Drosophila subauraria, Drosophila tani, Drosophila trapezifrons, Drosophila triauraria, Drosophila truncata, Drosophila vulcana, Drosophila watanabei, Drosophila fuyamai, Drosophila biarmipes, Drosophila mimetica, Drosophila pulchrella, Drosophila suzukii, Drosophila unipectinata, Drosophila lutescens, Drosophila paralutea, Drosophila prostipennis, Drosophila takahashii, Drosophila trilutea, Drosophila bifasciata, Drosophila imaii, Drosophila pseudoobscura, Drosophila saltans, Drosophila sturtevanti, Drosophila nebulosa, Drosophila paulistorum, and Drosophila willistoni. In one embodiment, the fly is Drosophila melanogaster.

As used herein, "amyloid-β peptide-42 (Aβ42)" and "Aβ42" are used interchangeably to refer to a 42-amino acid polypeptide that is produced in nature through the proteolytic cleavage of human amyloid precursor protein (APP) by beta and gamma s. Aβ42 is a major component of extracellular amyloid plaque depositions found in neuronal tissue of Alzheimer's disease patients. In the present invention, "amyloid-β peptide-42" includes a peptide encoded by a recombinant DNA wherein a nucleotide sequence encoding Aβ42 is operatively linked to an expression control sequence such that the Aβ42 peptide is produced in the absence of cleavage of APP by beta and gamma secretases. Examples of Aβ42 sequences include, but are not limited to, the sequences identified in FIG. 1 by SEQ ID NOs: 1 (amino acid sequence), and 2 (nucleotide sequence). It is noted that, because of the degeneracy of the genetic code, different nucleotide sequences can encode the same polypeptide sequence. The invention further contemplates, as equivalents of these Aβ42 sequences, mutant sequences that retain the biological effect of Aβ42 of forming amyloid plaque depositions.

As used herein, the term "amyloid plaque depositions" refers to insoluble protein aggregates that are formed extracellularly by the accumulation of amyloid peptides, such as Aβ42.

As used herein, the term "signal peptide" refers to a short amino acid sequence, typically less than 20 amino acids in length, that directs proteins to or through the endoplasmic reticulum secretory pathway of Drosophila. "Signal peptides" include, but are not limited to, the Drosophila signal peptides of Dint protein synonymous to "wingless (wg) signal peptide" (SEQ ID NO: 5) and the "Argos (aos) signal peptide" (SEQ ID NO: 7), the Drosophila Appl (SEQ ID NO: 9), presenilin (SEQ ID NO: 10), or windbeutel (SEQ ID NO: 11). Any conventional signal sequence that directs proteins through the endoplasmic reticulum secretory pathway, including variants of the above mentioned signal peptides, can be used in the present invention.

As used herein, an "amino acid linker" refers to a short amino acid sequence from about 2 to 10 amino acids in length that is flanked by two individual peptides.

As used herein, the term "tau protein" refers to the microtubule-associated protein Tau that is involved in microtubule assembly and stabilization. In neuronal tissues of Alzheimer's disease patients, Tau is found in intracellular depositions of neurofibrillary tangles. The human gene that encodes the human Tau protein contains 11 exons, and is described by Andreadis, A. et al., Biochemistry, 31 (43):10626-10633 (1992), herein incorporated by reference. In adult human brain, six tau isoforms are produced from a single gene by alternative mRNA splicing. They differ from each other by the presence or absence of 29- or 58-amino-acid inserts located in the amino-terminal half and 31-amino acid repeat located in the carboxyl-terminal half. Inclusion of the latter, which is encoded by exon 10 of the tau gene, gives rise to the three tau isoforms which each have 4 repeats. As used herein, the term "Tau protein" includes Tau isoforms produced by alternative mRNA splicing as well as mutant forms of human Tau proteins as described in SEQ ID NO: 2, SEQ ID: 12, SEQ ID: 13, SEQ ID: 14, and SEQ ID 15. In one embodiment, the Tau protein used to generate the double transgenic fly is represented by SEQ ID NOs: 3 (amino acid sequence) and 4 (nucleotide sequence). In the normal cerebral cortex, there is a slight preponderance of 3 repeat over 4 repeat tau isoforms. These repeats and some adjoining sequences constitute the microtubule-binding domain of tau (Goedert, et al., 1998 Neuron 21, 955-958). In neuronal tissues of Alzheimer's disease patients, Tau is hyperphosphorylated and adopts abnormal and/or pathological conformations detectable using conformational-dependent antibodies, such as MCI and ALZ50 (Jicha G. A., et al., Journal of Neuroscience Research 48:128-132 (1997)). Thus, "Tau protein", as used herein, includes Tau protein recognized by these conformation specific-antibodies.

The invention further contemplates, as equivalents of these Tau sequences, mutant sequences that retain the biological effect of Tau of forming neurofibrillary tangles. Therefore, "Tau protein", as used herein, also includes Tau proteins containing mutations and variants. These mutations include but are not limited to: Exon 10+12 "Kumamoto pedigree" (Yasuda et al., (2000) Ann Neurol. 47: 422-9); I260V (Grover et al., Exp Neurol. 2003 November; 184(1):131-40); G272V (Hutton et al., 1998 Nature 393:702-5; Heutink et al., (1997) Ann Neurol. 41(2):150-9; Spillantini et al., (1996) Acta Neuropathol (Berl). 1996 July; 92(1):42-8); N279K (Clark et al., (1998). Proc Natl Acad Sci USA 95: 13103-13107; D'Souza et al., (1999) Proc Natl Acad Sci USA. 96: 5598-5603; Reed et al., (1997) Ann Neurol. 1997 42:564-72; Hasegawa et al., (1999) FEBS Letters 443: 93-96; Hong et al., (1998) Science 282: 1914-1917); delK280 (Rizzu et al., (1999) Am J Hum Genet 64: 414-421; D'Souza et al., (1999) Proc Natl Acad Sci USA. 96: 5598-5603) L284L (D'Souza et al., (1999) Proc Natl Acad Sci USA. 96: 5598-5603); P301L (Hutton et al., 1998 Nature 393:702-5; Heutink et al., (1997) Ann Neurol. 41(2):150-9; Spillantini et al., (1996) Acta Neuropathol (Berl). 1996 July; 92(1):42-8; Hasegawa et al., (1998) FEBS Lett. 1998 437(3):207-101; Nacharaju et al., (1999) FEBS Letters 447: 195-199); P301S Bugiani (1999) J Neuropathol Exp Neurol. 58:667-77; Goedert et al., (1999) FEBS Letters 450: 306-311); S305N (Iijima et al., (1999) Neuroreport 10: 497-501; Hasegawa et al., (1998) FEBS Lett. 1998 437(3): 207-101; D'Souza et al., (1999) Proc Natl Acad Sci USA. 96: 5598-5603; S305S (Stanford et al., Brain, 123, 880-893, 2000) S305S (Wszolek et al., Brain. 2001 124:1666-70); V337M (Poorkaj et al., (1998) Ann Neurol. 1998 43:815-25;

Spillantini et al., (1998) American Journal of Pathology 153: 1359-1363; Sumi et al., (1992) Neurology. 42:120-7; Hasegawa et al., (1998) FEBS Lett. 1998 437(3):207-10); G389R (Murrell et al., J Neuropathol Exp Neurol. 1999 December; 58(12):1207-26; Pickering-Brown, et al., Ann Neurol. 2000 48(6):859-67); R406W (Hutton et al., 1998 Nature 393:702-5; Reed et al., (1997) Ann Neurol. 1997 42:564-72; Hasegawa et al., (1998) FEBS Lett. 1998 437(3):207-101); 3'Ex10+3, GtoA (Spillantini et al., (1998) American Journal of Pathology 153: 1359-1363; Spillantini et al., (1997) Proc Natl Acad Sci USA. 199794(8):4113-8); 3'Ex10+16 (Baker et al., (1997) Annals of Neurology 42: 794-798; Goedert et al., (1999b) Nature Medicine 5: 454-457; Hutton et al., (1998) Nature 393: 702-705); 3'Ex10+14 (Hutton et al., (1998) Nature 393: 702-705; Lynch et al., (1994) Neurology 44:1878-1884); 3'Ex10+13 (Hutton et al., (1998) Nature 393: 702-705).

Many human Tau gene sequences exist. In adult human brain, six tau isoforms are produced from a single gene by alternative mRNA splicing (Goedert et al., Neuron. 1989 3:519-26). It is noted that, because of the degeneracy of the genetic code, different nucleotide sequences can encode the same polypeptide sequence. The invention further contemplates the use of Tau genes containing sequence polymorphisms (See, for example, Table 1).

TABLE 1

Polymorphisms identified within the human Tau gene. Underlined polymorgphims are inherited as a part of extended haplotype 2. In case of exons skipped in the brain mRNA (exon 4a, 6, 8) locations of polymorphic sites are counted from the first nucleotide of the exon.

| Exon/Intron | Polymorphisms |
| --- | --- |
| E1 | 5'UTR–13 a--> g |
| I1 | nt–93 t --> c |
| I2 | nt+18 c --> t |
| I3 | nt+9 a --> g |
| I3 | nt–103 t --> a (very rare on H1) |
| I3 | nt–94a -->t (very rare on H1) |
| E4a | n+232 C --> T (CCG/CTG; P/L) |
| E4a | n+480 G --> A (GAC/AAC; R/N) |
| E4a | n+482 C --> T (GAC/GAT; N/N) |
| E4a | n+493 T --> C (GTA/GCA; V/A) |
| E4a | n316 A --> G (CAA/CGA, Q/Q) |
| I4a | nt–72 t --> c |
| E6 | n+139 C --> T (CAC/TAC H/Y) (very common) |
| E6 | n+157 T --> C(ACT/ACC S/P) |
| I6 | nt+67 a --> g |
| I6 | nt+105 t --> c |
| E7 | P176P (G --> A) |
| E8 | n+5 T --> C (ACT/ACC, T/T) |
| I8 | nt–26 g --> a |
| E9 | A227A (GCA/GCG) |
| E9 | N255N (AAT/AAC) |
| E9 | P270P (CCG/CCA) |
| I9 | nt–47 c --> a (very rare on H1) |
| I9 | Δ238bp |
| I11 | nt+34 g --> a |
| I11 | nt+90 g --> a |
| I11 | nt+296 c -->t |
| I13 | nt+34 t --> c |

The invention also contemplates the use of Tau proteins or genes from other animals, including but not limited to mice (Lee et al., (1988) Science 239, 285-8), rats (Goedert et al., (1992) Proc. Natl. Acad. Sci. U.S.A. 89 (5), 1983-1987), *Bos taurus* (Himmler et al., (1989) Mol. Cell. Biol. 9 (4), 1381-1388), *Drosophila melanogaster* (Heidary & Fortini, (2001) Mech. Dev. 108 (1-2), 171-178) and *Xenopus laevis* (Olesen et al., (2002) Gene 283 (1-2), 299-309). The Tau genes from other animals may additionally contain mutations equivalent to those previously described. Equivalent positions can be identified by sequence alignment, and equivalent mutations can be introduced by means of site-directed mutagenesis or other means known in the art.

As used herein, the term "neurofibrillary tangles" refers to insoluble twisted fibers that form intracellularly and that are composed mainly of Tau protein.

As used herein, the term "operatively linked" refers to a juxtaposition wherein the components described are in a relationship permitting them to function in their intended manner. An expression control sequence "operatively linked" to a coding sequence is ligated in such a way that expression of the coding sequence is achieved under conditions compatible with the activity of the control sequences.

As used herein, the term "expression control sequence" refers to promoters, enhancer elements, and other nucleic acid sequences that contribute to the regulated expression of a given nucleic acid sequence. The term "promoter" refers to DNA sequences recognized by RNA polymerase during initiation of transcription and can include enhancer elements. As used herein, the term "enhancer element" refers to a cis-acting nucleic acid element, which controls transcription initiation from homologous as well as heterologous promoters independent of distance and orientation. Preferably, an "enhancer element" also controls the tissue and temporal specification of transcription initiation. In particular embodiments, enhancer elements include, but are not limited to, the UAS control element. "UAS" as used herein, refers to an Upstream Activating Sequence recognized and bound by the Gal4 transcriptional activator. The term "UAS control element", as used herein, refers to a UAS element that is activated by Gal4 transcriptional regulator protein. A "tissue specific" expression control sequence, as used herein, refers to expression control sequences that drive expression in one tissue or a subset of tissues, while being essentially inactive in at least one other tissue. "Essentially inactive" means that the expression of a sequence operatively linked to a tissue specific expression control sequence is less than 5% of the level of expression of that sequence in that tissue where the expression control sequence is most active. Preferably, the level of expression in the tissue is less than 1% of the maximal activity, or there is no detectable expression of the sequence in the tissue. "Tissue specific expression control sequences" include those that are specific for organs such as the eye, wing, notum, brain, as well as tissues of the central and peripheral nervous systems. Examples of tissue specific control sequences include, but are not limited to, the sevenless promoter/enhancer (Bowtell et al., Genes Dev. 2(6):620-34 (1988)); the eyeless promoter/enhancer (Bowtell et al., Proc. Natl. Acad. Sci. U.S.A. 88(15):6853-7 (1991)); gmr/glass responsive promoters/enhancers (Quiring et al., Science 265: 785-9 (1994)), and promoters/enhancers derived from any of the rhodopsin genes, that are useful for expression in the eye; enhancers/promoters derived from the dpp or vestigial genes useful for expression in the wing (Staehling-Hampton et al., Cell Growth Differ. 5(6):585-93 (1994)); Kim et al., Nature 382:133-8 (1996)); promoters/enhancers derived from elav (Yao and White, J. Neurochem. 63(1):41-51 (1994)), *Appl* (Martin-Morris and White, Development 110(1): 185-95 (1990)), and nirvana (Sun et al., Proc. Nat'l Acad. Sci. U.S.A. 96: 10438-43 (1999)) genes useful for expression in the central nervous system; and promoters/enhancers derived from neural specific D42 genes, all of which references are incorporated by reference herein. Other examples of expression control sequences include, but are not limited to the heat shock promoters/enhancers from the hsp70 and hsp83 genes, useful for temperature induced expression; and promoters/ enhancers derived from ubiquitously expressed genes, such as tubulin, actin, or ubiquitin.

As used herein, the term "phenotype" refers to an observable and/or measurable physical, behavioral, or biochemical characteristic of a fly. The term "altered phenotype" as used herein, refers to a phenotype that has changed relative to the phenotype of a wild-type fly. Examples of altered phenotypes include a behavioral phenotype, such as appetite, mating behavior, and/or life span, that has changed by a measurable amount, e.g. by at least 10%, 20%, 30%, 40%, or more preferably 50%, relative to the phenotype of a control fly; or a morphological phenotype that has changed in an observable way, e.g. different growth rate of the fly; or different shape, size, color, or location of an organ or appendage; or different distribution, and/or characteristic of a tissue, as compared to the shape, size, color, location of organs or appendages, or distribution or characteristic of a tissue observed in a control fly. As used herein, "a synergistic altered phenotype" or "synergistic phenotype," refers to a phenotype wherein a measurable and/or observable physical, behavioral, or biochemical characteristic of a fly is more than the sum of its components.

A "change in phenotype" or "change in altered phenotype," as used herein, means a measurable and/or observable change in a phenotype relative to the phenotype of a control fly.

As used herein, a "control fly" refers to a larval or adult fly of the same genotype of the transgenic fly as to which it is compared, except that the control fly either i) does not comprise one or both of the transgenes present in the transgenic fly, or ii) has not been administered a candidate agent.

As used herein, the term "candidate agent" refers to a biological or chemical compound that when administered to a transgenic fly has the potential to modify the phenotype of the fly, e.g. partial or complete reversion of the altered phenotype towards the phenotype of a wild type fly. "Agents" as used herein can include any recombinant, modified or natural nucleic acid molecule, library of recombinant, modified or natural nucleic acid molecules, synthetic, modified or natural peptide, library of synthetic, modified or natural peptides; and any organic or inorganic compound, including small molecules, or library of organic or inorganic compounds, including small molecules.

As used herein, the term "small molecule" refers to compounds having a molecular mass of less than 3000 Daltons, preferably less than 2000 or 1500, more preferably less than 1000, and most preferably less than 600 Daltons. Preferably but not necessarily, a small molecule is a compound other than an oligopeptide.

As used herein, a "therapeutic agent" refers to an agent that ameliorates one or more of the symptoms of a neurodegenerative disorder such as Alzheimer's disease in mammals, particularly humans. A therapeutic agent can reduce one or more symptoms of the disorder, delay onset of one or more symptoms, or prevent or cure the disease. As used herein, the "rough eye" phenotype is characterized by irregular ommatidial packing, occasional ommatidial fusions, and missing bristles that can be caused by degeneration of neuronal cells. The eye becomes rough in texture relative to its appearance in wild type flies, and can be easily observed by microscope.

As used herein, the "concave wing" phenotype is characterized by abnormal folding of the fly wing such that wings are bent upwards along their long margins.

As used herein, "locomotor dysfunction" refers to a phenotype where flies have a deficit in motor activity or movement (e.g., at least a 10% difference in a measurable parameter) as compared to control flies. Motor activities include flying, climbing, crawling, and turning. In addition, movement traits where a deficit can be measured include, but are not limited to: i) average total distance traveled over a defined period of time; ii) average distance traveled in one direction over a defined period of time; iii) average speed (average total distance moved per time unit); iv) distance moved in one direction per time unit; v) acceleration (the rate of change of velocity with respect to time; vi) turning; vii) stumbling; viii) spatial position of a fly to a particular defined area or point; ix) path shape of the moving fly; and x) undulations during larval movement; xi) rearing or raising of larval head; and xii) larval tail flick. Examples of movement traits characterized by spatial position include, without limitation: (1) average time spent within a zone of interest (e.g., time spent in bottom, center, or top of a container; number of visits to a defined zone within container); and (2) average distance between a fly and a point of interest (e.g., the center of a zone). Examples of path shape traits include the following: (1) angular velocity (average speed of change in direction of movement); (2) turning (angle between the movement vectors of two consecutive sample intervals); (3) frequency of turning (average amount of turning per unit of time); and (4) stumbling or meander (change in direction of movement relative to the distance). Turning parameters can include smooth movements in turning (as defined by small degrees rotated) and/or rough movements in turning (as defined by large degrees rotated).

I. Generation of Transgenic *Drosophila*

A double transgenic fly that carries both a transgene that encodes Tau protein and a transgene that encodes human Aβ42 peptide is disclosed. The Aβ42/Tau double transgenic fly provides an improved model for neurodegenerative disorders such as Alzheimer's disease, which is characterized by an extracellular accumulation of Aβ42 peptide and an intracellular deposition of a hyperphosphorylated form of microtubule-associated protein Tau. Because of the presence of these two transgenes, the double transgenic fly of the present invention can be used to screen for therapeutic agents effective in the treatment of Alzheimer's disease.

A. General

The transgenic flies of the present invention can be generated by any means known to those skilled in the art. Methods for production and analysis of transgenic *Drosophila* strains are well established and described in Brand et al., Methods in Cell Biology 44:635-654 (1994); Hay et al., Proc. Natl. Acad. Sci. USA 94(10):5195-200 (1997); and in Robert D. B. *Drosophila: A Practical Approach*, Washington D.C. (1986), herein incorporated by reference in their entireties.

In general, to generate a transgenic fly, a transgene of interest is stably incorporated into a fly genome. Any fly can be used, however a preferred fly of the present invention is a member of the Drosophilidae family. An exemplary fly is *Drosophila Melanogaster*.

A variety of transformation vectors are useful for the generation of the transgenic flies of the present invention, and include, but are not limited to, vectors that contain transposon sequences, which mediate random integration of transgene into the genome, as well as vectors that use homologous recombination (Rong and Golic, Science 288: 2013-2018 (2000)). A preferred vector of the present invention is pUAST (Brand and Perrimon, Development 118:401-415 (1993)) that contains sequences from the transposable P-element which mediate insertion of a transgene of interest into the fly genome. Another preferred vector is PdL that is able to yield doxycycline-dependent overexpression (Nandis, Bhole and Tower, Genome Biology 4 (R8): 1-14, (2003)).

P-element transposon mediated transformation is a commonly used technology for the generation of transgenic flies and is described in detail in Spradling, P element mediated transformation, In *Drosophila: A Practical Approach* (ed. D. B. Roberts), pp #175-197, IRL Press, Oxford, UK (1986), herein incorporated by reference. Other transformation vectors based on transposable elements, include for example, the hobo element (Blackman et al., Embo J. 8(1):211-7 (1989)), mariner element (Lidholm et al., Genetics 134(3):859-68 (1993)), the hermes element (O'Brochta et al., Genetics 142 (3):907-14 (1996)), Minos (Loukeris et al., Proc. Natl. Acad. Sci. USA 92(21):9485-9 (1995)), or the PiggyBac element (Handler et al., Proc. Natl. Acad. Sci. USA 95(13):7520-5 (1998)). In general, the terminal repeat sequences of the transposon that are required for transposition are incorporated into a transformation vector and arranged such that the terminal repeat sequences flank the transgene of interest. It is preferred that the transformation vector contains a marker gene used to identify transgenic animals. Commonly used, marker genes affect the eye color of *Drosophila*, such as derivatives of the *Drosophila* white gene (Pirrotta V., & C. Brockl, EMBO J. 3(3):563-8 (1984)) or the *Drosophila* rosy gene (Doyle W. et al., Eur. J. Biochem. 239(3):782-95 (1996)) genes. Any gene that results in a reliable and easily measured phenotypic change in transgenic animals can be used as a marker. Examples of other marker genes used for transformation include the yellow gene (Wittkopp P. et al., Curr Biol. 12(18):1547-56 (2002)) that alters bristle and cuticle pigmentation; the forked gene (McLachlan A., Mol Cell Biol. 6(1): 1-6 (1986)) that alters bristle morphology; the Adh+ gene used as a selectable marker for the transformation of Adh− strains (McNabb S. et al., Genetics 143(2):897-911 (1996)); the Ddc+ gene used to transform Ddc$^{ts2}$ mutant strains (Scholnick S. et al., Cell 34(1):37-45(1983)); the lacZ gene of *E. coli*; the neomycin$^R$ gene from the *E. coli* transposon Tn5; and the green fluorescent protein (GFP; Handler and Harrell, Insect Molecular Biology 8:449-457 (1999)), which can be under the control of different promoter/enhancer elements, e.g. eyes, antenna, wing and leg specific promoter/enhancers, or the poly-ubiquitin promoter/enhancer elements.

Plasmid constructs for introduction of the desired transgene are coinjected into *Drosophila* embryos having an appropriate genetic background, along with a helper plasmid that expresses the specific transposase needed to mobilized the transgene into the genomic DNA. Animals arising from the injected embryos (G0 adults) are selected, or screened manually, for transgenic mosaic animals based on expression of the marker gene phenotype and are subsequently crossed to generate fully transgenic animals (G1 and subsequent generations) that will stably carry one or more copies of the transgene of interest.

Binary systems are commonly used for the generation of transgenic flies, such as the UAS/GAL4 system. This system is a well-established which employs the UAS upstream regulatory sequence for control of promoters by the yeast GAL4 transcriptional activator protein, as described in Brand and Perrimon, Development 118(2):401-15 (1993)) and Rorth et al, Development 125(6):1049-1057 (1998), herein incorporated by reference in their entireties. In this approach, transgenic *Drosophila*, termed "target" lines, are generated where the gene of interest (e.g. Aβ42 or TAU)) is operatively linked to an appropriate promoter controlled by UAS. Other transgenic *Drosophila* strains, termed "driver" lines, are generated where the GAL4 coding region is operatively linked to promoters/enhancers that direct the expression of the GAL4 activator protein in specific tissues, such as the eye, antenna, wing, or nervous system. The gene of interest is not expressed in the "target" lines for lack of a transcriptional activator to "drive" transcription from the promoter joined to the gene of interest. However, when the UAS-target line is crossed with a GAL4 driver line, the gene of interest is induced. The resultant progeny display a specific pattern of expression that is characteristic for the GAL4 line.

The technical simplicity of this approach makes it possible to sample the effects of directed expression of the gene of interest in a wide variety of tissues by generating one transgenic target line with the gene of interest, and crossing that target line with a panel of pre-existing driver lines. Individual GAL4 driver *Drosophila* strains with specific drivers have been established and are available for use (Brand and Perrimon, Development 118(2):401-15 (1993)). Driver strains include, for example apterous-Gal4 (wings, brain, interneurons), elav-Gal4 (CNS), sevenless-Gal4, eyeless-Gal4, GMR-Gal4 (eyes) and the brain specific 7B-Gal4 driver.

B. Generation of Aβ42/Tau Double Transgenic

The present invention discloses a double transgenic fly that has incorporated into its genome a DNA sequence that encodes Aβ42 fused to a signal peptide, and a DNA sequence that encodes Tau protein.

To generate the double transgenic fly, transgenic *Drosophila* that express either the Aβ42 or the Tau protein are independently made and then crossed to generate a *Drosophila* that expresses both proteins.

In a preferred embodiment, transgenic *Drosophila* are produced using the UAS/GAL4 control system. Briefly, to generate a transgenic fly that expresses Tau, a DNA sequence encoding Tau is cloned into a vector such that the sequence is operatively linked to the GAL4 responsive element UAS. Vectors containing UAS elements are commercially available, such as the pUAST vector (Brand and Perrimon, Development 118:401-415 (1993)), which places the UAS sequence element upstream of the transcribed region. The DNA is cloned using standard methods (Sambrook et al., *Molecular Biology: A laboratory Approach*, Cold Spring Harbor, N.Y. (1989); Ausubel, et al., *Current protocols in Molecular Biology*, Greene Publishing, Y, (1995)) and is described in more detail under the Molecular Techniques section of the present application. After cloning the DNA into appropriate vector, such as pUAST, the vector is injected into *Drosophila* embryos (e.g. yw embryos) by standard procedures (Brand et al., Methods in Cell Biology 44:635-654 (1994)); Hay et al., Proc. Natl. Acad. Sci. USA 94(10):5195-200 (1997) to generate transgenic *Drosophila*.

When the binary UAS/GAL4 system is used, the transgenic progeny can be crossed with *Drosophila* driver strains to assess the presence of an altered phenotype. A preferred *Drosophila* comprises the eye specific driver strain gmr-GAL4, which enables identification and classification of transgenic flies based on the severity of the rough eye phenotype. Expression of Tau in *Drosophila* eye results in the rough eye phenotype (characterized by an eye with irregular ommatidial packing, occasional ommatidial fusions, and missing bristles), which can be easily observed by microscope. The severity of the rough eye phenotype exhibited by a transgenic line, can be classified as strong, medium, or weak. The weak or mild lines have a rough, disorganized appearance covering the ventral portion of the eye. The medium severity lines show greater roughness over the entire eye, while in strong severity lines the entire eye seems to have lost/fused many of the ommatidia and interommatidial bristles, and the entire eye has a smooth, glossy appearance.

To generate a transgenic fly that expresses human Aβ42, a DNA sequence encoding human Aβ42 is ligated in frame to a DNA sequence encoding a signal peptide such that the Aβ42 peptide can be exported across cell membranes. The signal sequence is directly linked to the Aβ42 coding sequence or indirectly linked by using a DNA linker sequence, for example of 3, 6, 9, 12, or 15 nucleotides. Any signal peptide that directs proteins to or through the endoplasmic reticulum secretory pathway of *Drosophila* is used. Preferred signal peptides of the present invention are the Argos (aos) signal peptide (SEQ ID NO: 7), the wingless (wg) signal peptide (SEQ ID NO: 5) the *Drosophila* Appl (SEQ ID NO: 9), presenilin (SEQ ID NO: 10), and windbeutel (SEQ ID NO: 11).

The DNA encoding the Aβ42 peptide is linked to a signal sequence by standard ligation techniques and is then cloned into a vector such that the sequence is operatively linked to the GAL4 responsive element UAS. A preferred transformation vector for the generation of Aβ42 transgenic flies is the pUAST vector (Brand and Perrimon, Development 118:401-415 (1993)). As described for the generation of Tau transgenic flies, the vector is injected into *Drosophila* embryos (e.g. yw embryos) by standard procedures (Brand et al., Meth. in Cell Biol. 44:635-654 (1994)); Hay et al., Proc. Natl. Acad. Sci. USA 94(10):5195-200 (1997)) and progeny are then selected and crossed based on the phenotype of the selected marker gene. When the binary UAS/GAL4 system is used, the transgenic progeny can be crossed with *Drosophila* driver strains to assess the presence of an altered phenotype. Preferred *Drosophila* driver strains are gmr-GAL4 (eye) and elav-GAL4 (CNS).

To assess an eye phenotype (e.g., rough eye phenotype) a gmr-GAL4 driver strain is used in the cross. Ectopic overexpression of Aβ42 in *Drosophila* eye is believed to disrupt the regular trapezoidal arrangement of the photoreceptor cells of the ommatidia (identical single units, forming the *Drosophila* compound eye), the severity of which is believed to depend on transgene copy number and expression levels. To evaluate a locomotor phenotype (e.g., climbing assay), an elav-Gal4 driver strain is used in the cross. Ectopic overexpression of Aβ42 in *Drosophila* central nervous system (CNS) is believed to result in locomotor deficiencies, such as impaired movement, climbing and flying.

Once the single transgenic flies are produced, the flies can be crossed with each other by mating. Flies are crossed according to conventional methods. When the binary UAS/GAL4 system is used, the fly is crossed with an appropriate driver strain and the altered phenotype assessed, as described above, transgenic flies are classified by assessing phenotypic severity. For example, as disclosed herein, the combination of Tau and Aβ42 transgenes is believed to produce a synergistic effect on the eye.

Expression of Tau and Aβ42 proteins in transgenic flies is confirmed by standard techniques, such as Western blot analysis or by immunostaining of *Drosophila* tissue cross-sections, both of which are described below.

a. Western Blot Analysis

Western blot analysis is performed by standard methods. Briefly, as means of example, to detect expression of the Aβ42 peptide or Tau by western blot analysis, whole flies, or *Drosophila* heads (e.g. 80-90 heads) are collected and placed in an eppendorf tube on dry ice containing 100 μl of 2% SDS, 30% sucrose, 0.718 M Bistris, 0.318 M Bicine, with "Complete" protease inhibitors (Boehringer Mannheim), then ground using a mechanical homogenizer. Samples are heated for 5 min at 95° C., spun down for 5 min at 12,000 rpm, and supernatants are transferred into a fresh eppendorf tube. 5% β-mercaptoethanol and 0.01% bromphenol blue are added and samples are boiled prior to loading on a separating gel. Approximately 200 ng of total protein extract is loaded for each sample, on a 15% Tricine/Tris SDS PAGE gel containing 8M Urea. After separating, samples are then transferred to PVDF membranes (BIO-RAD, 162-0174) and the membranes are subsequently boiled in PBS for 3 min. Anti-Tau antibody (e.g. T14 (Zymed) and AT100 (Pierce-Endogen) or anti-β42 antibody (e.g. 6E10 (Senetek PLC Napa, Calif.) are hybridized, generally at a concentration of 1:2000, in 5% non-fat milk, 1×PBS containing 0.1% Tween 20, for 90 min at room temperature. Samples are washed 3 times for 5 min., 15 min. and 15 min. each, in 1×PBS-0.1% Tween-20. Labeled secondary antibody, (for example, anti-mouse-HRP from Amersham Pharmacia Biotech, NA 931) is prepared, typically at a concentration of 1:2000, in 5% non-fat milk, 1×PBS containing 0.1% Tween 20, for 90 min at room temperature. Samples are then washed 3 times for 5 min., 15 min. and 15 min. each, in 1×PBS-0.1% Tween-20. Protein is then detected using the appropriate method. For example, when anti-mouse-HRP is used as the conjugated secondary antibody, ECL (ECL Western Blotting Detection Reagents, Amersham Pharmacia Biotech, # RPN 2209) is used for detection.

b. Cross Sections

As a manner of confirming protein expression in transgenic flies, immunostaining of *Drosophila* organ cross sections is performed. Such a method is of particular use to confirm the presence of hyperphosphorylated Tau, which is a modified form of the Tau protein that is present in non-diseased tissue. Hyperphosphorylated Tau exhibits altered pathological conformations as compared to Tau protein and is present in diseased tissue from patients with certain neurodegenerative disorders, such as Alzheimer's disease.

Cross sections of *Drosophila* organs can be made by any conventional cryosectioning, such as the method described in Wolff, *Drosophila* Protocols, CSHL Press (2000), herein incorporated by reference. Cryosections can then be immunostained for detection of Tau and Aβ42 peptides using methods well known in the art. In a preferred embodiment, the Vectastain ABC Kit (which comprises biotinylated anti-mouse IgG secondary antibody, and avidin/biotin conjugated to the enzyme Horseradish peroxidase H (Vector Laboratories) is used to identify the protein. In other embodiments the secondary antibody is conjugated to a fluorophore. Briefly, cryosections are blocked using normal horse serum, according to the Vectastain ABC Kit protocol. The primary antibody, recognizing the human Aβ42 peptide or Tau, is typically used at a dilution of 1:3000 and incubation with the secondary antibody is done in PBS/1% BSA containing 1-2% normal horse serum, also according to the Vectastain ABC Kit protocol. The procedure for the ABC Kit is followed; incubations with the ABC reagent are done in PBS/0.1% saponin, followed by 4×10 minute washes in PBS/0.1% saponin. Sections are then incubated in 0.5 ml per slide of the Horseradish Peroxidase H substrate solution, 400 μg/ml 3,3'-diaminobenzidene (DAB), 0.006% H 2O2 in PBS/0.1% saponin, and the reaction is stopped after 3 min. with 0.02% sodium azide in PBS. Sections are rinsed several times in PBS and dehydrated through an ethanol series before mounting in DPX (Fluka).

Exemplary antibodies that can be used to immunostain cross sections include but are not limited to, the monoclonal antibody 6E10 (Senetek PLC Napa, Calif.) that recognizes Aβ42 peptide and anti-Tau antibodies ALZ50 and MCI (Jicha Ga., et al., J. of Neurosci. Res. 48:128-132 (1997)).

Alternatively, antibodies for use in the present invention that recognize Aβ42 and Tau can be made using standard protocols known in the art (See, for example, Antibodies: A Laboratory Manual ed. by Harlow and Lane (Cold Spring Harbor Press: 1988)). A mammal, such as a mouse, hamster, or rabbit can be immunized with an immunogenic form of the protein (e.g., a Aβ42 or Tau polypeptide or an antigenic fragment which is capable of eliciting an antibody response). Immunogens for raising antibodies are prepared by mixing the polypeptides (e.g., isolated recombinant polypeptides or synthetic peptides) with adjuvants. Alternatively, Aβ42 or Tau polypeptides or peptides are made as fusion proteins to larger immunogenic proteins. Polypeptides can also be covalently linked to other larger immunogenic proteins, such as keyhole limpet hemocyanin. Alternatively, plasmid or viral vectors encoding Aβ42 or Tau, or a fragment of these proteins, can be used to express the polypeptides and generate an immune response in an animal as described in Costagliola et al., J. Clin. Invest. 105:803-811 (2000), which is incorporated herein by reference. In order to raise antibodies, immunogens are typically administered intradermally, subcutaneously, or intramuscularly to experimental animals such as rabbits, sheep, and mice. In addition to the antibodies discussed above, genetically engineered antibody derivatives can be made, such as single chain antibodies.

The progress of immunization can be monitored by detection of antibody titers in plasma or serum. Standard ELISA, flow cytometry or other immunoassays can also be used with the immunogen as antigen to assess the levels of antibodies. Antibody preparations can be simply serum from an immunized animal, or if desired, polyclonal antibodies can be isolated from the serum by, for example, affinity chromatography using immobilized immunogen.

To produce monoclonal antibodies, antibody-producing splenocytes can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, Nature, 256: 495-497 (1975)), the human B cell hybridoma technique (Kozbar et al., Immunology Today, 4: 72 (1983)), and the EBV-hybridoma technique to produce human monoclonal antibodies (Cole et al., Monoclonal Antibodies and Cancer Therapy, Alan R. Liss, Inc. pp. 77-96(1985)). Hybridoma cells can be screened immunochemically for production of antibodies that are specifically reactive with Aβ42 or Tau peptide, or polypeptide, and monoclonal antibodies isolated from the media of a culture comprising such hybridoma cells.

II. Molecular Techniques

In the present invention, DNA sequences that encode Tau or human Aβ42 are cloned into transformation vectors suitable for the generation of transgenic flies.

A. Generation of DNA Sequences Encoding Tau or Human Aβ42

DNA sequences encoding Tau and Aβ42 can be obtained from genomic DNA or be generated by synthetic means using methods well known in the art (Sambrook et al., *Molecular Biology: A laboratory Approach*, Cold Spring Harbor, N.Y. (1989); Ausubel, et al., *Current protocols in Molecular Biology*, Greene Publishing, Y, (1995)). Briefly, human genomic DNA can be isolated from peripheral blood or mucosal scrapings by phenol extraction, or by extraction with kits such as the QIAamp Tissue kit (Qiagen, Chatsworth, Cal.), Wizard genomic DNA purification kit (Promega, Madison, Wis.), and the ASAP genomic DNA isolation kit (Boehringer Mannheim, Indianapolis, Ind.). DNA sequences encoding Tau and Aβ42 can then be amplified from genomic DNA by polymerase chain reaction (PCR) (Mullis and Faloona *Methods Enzymol.*, 155: 335 (1987)), herein incorporated by reference) and cloned into a suitable recombinant cloning vector.

Alternatively, a cDNA that encodes Tau or human Aβ42 can be amplified from mRNA using RT-PCR and cloned into a suitable recombinant cloning vector. RNA may be prepared by any number of methods known in the art; the choice may depend on the source of the sample. Methods for preparing RNA are described in Davis et al., Basic Methods in Molecular Biology, Elsevier, N.Y., Chapter 11 (1986); Ausubel et al., Current Protocols in Molecular Biology, Chapter 4, John Wiley and Sons, NY (1987); Kawasaki and Wang, PCR Technology, ed. Erlich, Stockton Press NY (1989); Kawasaki, PCR Protocols: A Guide to Methods and Applications, Innis et al. eds. Academic Press, San Diego (1990); all of which are incorporated herein by reference.

It is preferred, following generation of sequences that encode Tau or Aβ42 by PCR or RT-PCR, that the sequences are cloned into an appropriate sequencing vector in order that the sequence of the cloned fragment can be confirmed by nucleic acid sequencing in both directions.

Suitable recombinant cloning vectors for use in the present invention contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. For example, the origin of replication from the plasmid pBR322 is suitable for most Gram-negative bacteria, the 2 micron plasmid origin is suitable for yeast, and various viral origins (e.g. SV40, adenovirus) are useful for cloning vectors in mammalian cells. Generally, the origin of replication is not needed for mammalian expression vectors unless these are used in mammalian cells able to replicate high levels of DNA, such as COS cells.

Advantageously, a cloning or expression vector may contain a selection gene also referred to as a selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Since cloning is most conveniently performed in *E. coli*, an *E. coli*-selectable marker, for example, the β-lactamase gene that confers resistance to the antibiotic ampicillin, is of use. These can be obtained from *E. coli* plasmids, such as pBR322 or a pUC plasmid such as pUC18 or pUC19.

Sequences that encode Tau or human Aβ42 can also be directly cloned into a transformation vector suitable for generation of transgenic *Drosophila* such as vectors that allow for the insertion of sequences in between transposable elements, or insertion downstream of an UAS element, such as pUAST. Vectors suitable for the generation of transgenic flies preferably contain marker genes such that the transgenic fly can be identified such as, the white gene, the rosy gene, the yellow gene, the forked gene, and others mentioned previously. Suitable vectors can also contain tissue specific control sequences as described earlier, such as, the sevenless promoter/enhancer, the eyeless promoter/enhancer, glass-responsive promoters (gmr)/enhancers useful for expression in the eye; and enhancers/promoters derived from the dpp or vestigial genes useful for expression in the wing.

Sequences that encode Tau or human Aβ42 are ligated into a recombinant vector in such a way that the expression control sequences are operatively linked to the coding sequence.

Herein, DNA sequences that encode Tau or human Aβ42 can be generated through the use of Polymerase chain reaction (PCR), or RT-PCR which uses RNA-directed DNA polymerase (e.g., reverse transcriptase) to synthesize cDNAs which is then used for PCR.

III. Phenotypes and Methods of Detecting Altered Phenotypes

A double transgenic fly according to the invention can exhibit an altered eye phenotype, of progressive neurodegeneration in the eye that leads to measurable morphological changes in the eye (Fernandez-Funez et al., Nature 408:101-106 (2000); Steffan et. al, Nature 413:739-743 (2001)). The Drosophila eye is composed of a regular trapezoidal arrangement of seven visible rhabdomeres produced by the photoreceptor neurons of each Drosophila ommatidium. A phenotypic eye mutant according to the invention leads to a progressive loss of rhabdomeres and subsequently a rough-textured eye. A rough textured eye phenotype is easily observed by microscope or video camera. In a screening assay for compounds which alter this phenotype, one may observe slowing of the photoreceptor degeneration and improvement of the rough-eye phenotype (Steffan et. al, Nature 413:739-743 (2001)).

Neuronal degeneration in the central nervous system will give rise to behavioral deficits, including but not limited to locomotor deficits, that can be assayed and quantitated in both larvae and adult Drosophila. For example, failure of Drosophila adult animals to climb in a standard climbing assay (see, e.g. Ganetzky and Flannagan, J. Exp. Gerontology 13:189-196 (1978); LeBourg and Lints, J. Gerontology 28:59-64 (1992)) is quantifiable, and indicative of the degree to which the animals have a motor deficit and neurodegeneration. Neurodegenerative phenotypes include, but are not limited to, progressive loss of neuromuscular control, e.g. of the wings; progressive degeneration of general coordination; progressive degeneration of locomotion, and progressive loss of appetite. Other aspects of Drosophila behavior that can be assayed include but are not limited to circadian behavioral rhythms, feeding behaviors, inhabituation to external stimuli, and odorant conditioning. All of these phenotypes are measured by one skilled in the art by standard visual observation of the fly.

Another neural degeneration phenotype, is a reduced life span, for example, the Drosophila life span can be reduced by 10-80%, e.g., approximately, 30%, 40%, 50%, 60%, or 70%. Any observable and/or measurable physical or biochemical characteristic of a fly is a phenotype that can be assessed according to the present invention. Transgenic flies can be produced by identifying flies that exhibit an altered phenotype as compared to control (e.g., wild-type flies, or flies in which the transgene is not expressed). Therapeutic agents can be identified by screening for agents, that upon administration, result in a change in an altered phenotype of the transgenic fly as compared to a transgenic fly that has not been administered a candidate agent.

A change in an altered phenotype includes either complete or partial reversion of the phenotype observed. Complete reversion is defined as the absence of the altered phenotype, or as 100% reversion of the phenotype to that phenotype observed in control flies. Partial reversion of an altered phenotype can be 5%, 10%, 20%, preferably 30%, more preferably 50%, and most preferably greater than 50% reversion to that phenotype observed in control flies. Example measurable parameters include, but are not limited to, size and shape of organs, such as the eye; distribution of tissues and organs; behavioral phenotypes (such as, appetite and mating); and locomotor ability, such as can be observed in a climbing assays. For example, in a climbing assay, locomotor ability can be assessed by placing flies in a vial, knocking them to the bottom of the vial, then counting the number of flies that climb past a given mark on the vial during a defined period of time. 100% locomotor activity of control flies is represented by the number of flies that climb past the given mark, while flies with an altered locomotor activity can have 80%, 70%, 60%, 50%, preferably less than 50%, or more preferably less than 30% of the activity observed in a control fly population. Locomotor phenotypes also can be assessed as described in provisional application 60/396,339, Methods for Identifying Biologically Active Agents, herein incorporated by reference.

Memory Assay

In Drosophila, the best characterized assay for associative learning and memory is an odor-avoidance behavioral task (T. Tully, et al. J. Comp. Physiol. A157, 263-277 (1985), incorporated herein by reference). This classical (Pavlovian) conditioning involves exposing the flies to two odors (the conditioned stimuli, or CS), one at a time, in succession. During one of these odor exposures (the CS+), the flies are simultaneously subjected to electric shock (the unconditioned stimulus, or US), whereas exposure to the other odor (the CS−) lacks this negative reinforcement. Following training, the flies are then placed at a 'choice point', where the odors come from opposite directions, and expected to decide which odor to avoid. By convention, learning is defined as the fly's performance when testing occurs immediately after training. A single training trial produces strong learning: a typical response is that >90% of the flies avoid the CS+. Performance of wild-type flies from this single-cycle training decays over a roughly 24-hour period until flies once again distribute evenly between the two odors. Flies can also form long-lasting associative olfactory memories, but normally this requires repetitive training regimens.

IV. Utility of Aβ42/Tau Double Transgenic Fly

A. Disease Model

A double transgenic fly of the invention provides a model for neurodegeneration as is found in human neurological diseases such as Alzheimer's and tauopathies, such as Amyotrophic lateral sclerosis/parkinsonism-dementia complex of Guam Argyrophilic grain dementia, Corticobasal degeneration, Dementia pugilistica, Diffuse neurofibrillary tangles with calcification, Frontotemporal dementia with Parkinsonism linked to chromosome 17 (FTDP-17), Pick's disease, Progressive subcortical gliosis, Progressive supranuclear palsy (PSP), Tangle only dementia, Creutzfeldt-Jakob disease, Down syndrome, Gerstmann-Sträussler-Scheinker disease, Hallervorden-Spatz disease, Myotonic dystrophy, Age-related memory impairment, Alzheimer's disease, Amyotrophic lateral sclerosis, Amyotrophic lateral/parkinsonism-dementia complex of Guam, Auto-immune conditions (e.g. Guillain-Barre syndrome, Lupus), Biswanger's disease, Brain and spinal tumors (including neurofibromatosis), Cerebral amyloid angiopathies (Journal of Alzheimer's Disease vol. 3, 65-73 (2001)), Cerebral palsy, Chronic fatigue syndrome, Creutzfeldt-Jacob disease (including variant form), Corticobasal degeneration, Conditions due to developmental dysfunction of the CNS parenchyma, Conditions due to developmental dysfunction of the cerebrovasculature, Dementia—multi infarct, Dementia—subcortical, Dementia with Lewy bodies, Dementia of human immunodeficiency virus (HIV), Dementia lacking distinct histology, Dendatorubopallidolusian atrophy, Diseases of the eye, ear and vestibular systems involving neurodegeneration (including macular degeneration and glaucoma), Down's syndrome, Dyskinesias (Paroxysmal) Dystonias, Essential tremor, Fahr's syndrome, Friedrich's ataxia, Fronto-temporal dementia and Parkinsonism linked to chromosome 17 (FTDP-17), Frontotemporal lobar degeneration, Frontal lobe dementia, Hepatic encephalopathy, Hereditary spastic paraplegia, Huntington's disease, Hydrocephalus, Pseudotumor Cerebri and other conditions involving CSF dysfunction, Gaucher's disease, Spinal Muscular Atrophy (Hirayama Disease, Werdnig-Hoffman Disease, Kugelberg-Welander Disease), Korsakoff's syndrome, Machado-Joseph disease, Mild cognitive impairment, Monomelic Amyotrophy, Motor neuron diseases, Multiple system atrophy, Multiple sclerosis and other demyelinating conditions (eg leukodystrophies), Myalgic encephalomyelitis, Myotonic dystrophy, Myoclonus Neurodegeneration induced by chemicals, drugs and toxins, Neurological manifestations of Aids including Aids dementia, Neurological conditions (any) arising from polyglutamine expansions, Neurological/cognitive manifestations and consequences of bacterial and/or virus infections, including but not restricted to enteroviruses, Niemann-Pick disease, Non-Guamanian motor neuron disease with neurofibrillary tangles, Non-ketotic hyperglycinemia, Olivoponto cerebellar atrophy, Opthalmic and otic conditions involving neurodegeneration, including macular degeneration and glaucoma, Parkinson's disease, Pick's disease, Polio myelitis including non-paralytic polio, Primary lateral sclerosis, Prion diseases including Creutzfeldt-Jakob disease, kuru, fatal familial insomnia, and Gerstmann-Straussler-Scheinker disease, prion protein cerebral amyloid angiopathy, Postencephalitic Parkinsonism, Post-polio syndrome, Prion protein cerebral amyloid angiopathy, Progressive muscular atrophy, Progressive bulbar palsy, Progressive supranuclear palsy, Restless leg syndrome, Rett syndrome, Sandhoff disease, Spasticity, Spino-bulbar muscular atrophy (Kennedy's disease), Spinocerebellar ataxias, Sporadic fronto-temporal dementias, Striatonigral degeneration, Subacute sclerosing panencephalitis, Sulphite oxidase deficiency, Sydenham's chorea, Tangle only dementia, Tay-Sach's disease, Tourette's syndrome, Transmissable spongiform encephalopathies, Vascular dementia, and Wilson disease.

B. Methods for Identifying Therapeutic Agents

The present invention further provides a method for identifying a therapeutic agent for neurodegenerative disease using the Aβ42/Tau double transgenic fly disclosed herein. As used herein, a "therapeutic agent" refers to an agent that ameliorates the symptoms of neurodegenerative disease as determined by a physician. For example, a therapeutic agent can reduce one or more symptoms of neurodegenerative disease, delay onset of one or more symptoms, or prevent, or cure.

To screen for a therapeutic agent effective against a neurodegenerative disorder such as disease, a candidate agent is administered to an Aβ42/Tau transgenic fly. The transgenic fly is then assayed for a change in the phenotype as compared to the phenotype displayed by an Aβ42/Tau transgenic fly that has not been administered a candidate agent. An observed change in phenotype is indicative of an agent that is useful for the treatment of disease.

A candidate agent can be administered by a variety of means. For example, an agent can be administered by applying the candidate agent to the *Drosophila* culture media, for example by mixing the agent in *Drosophila* food, such as a yeast paste that can be added to *Drosophila* cultures. Alternatively, the candidate agent can be prepared in a 1% sucrose solution, and the solution fed to *Drosophila* for a specified time, such as 10 hours, 12 hours, 24 hours, 48 hours, or 72 hours. In one embodiment, the candidate agent is microinjected into *Drosophila* hemolymph, as described in WO 00/37938, published Jun. 29, 2000. Other modes of administration include aerosol delivery, for example, by vaporization of the candidate agent.

The candidate agent can be administered at any stage of *Drosophila* development including fertilized eggs, embryonic, larval and adult stages. In a preferred embodiment, the candidate agent is administered to an adult fly. More preferably, the candidate agent is administered during a larval stage, for example by adding the agent to the *Drosophila* culture at the third larval instar stage, which is the main larval stage in which eye development takes place.

The agent can be administered in a single dose or multiple doses. Appropriate concentrations can be determined by one skilled in the art, and will depend upon the biological and chemical properties of the agent, as well as the method of administration. For example, concentrations of candidate agents can range from 0.0001 µM to 1000 µM when delivered orally or through injection, 0.001 µM to 100 µM, 0.01 µm-10 µM, or 0.1 µM to 1 µM.

For efficiency of screening the candidate agents, in addition to screening with individual candidate agents, the candidate agents can be administered as a mixture or population of agents, for example a library of agents. As used herein, a "library" of agents is characterized by a mixture more than 20, 100, $10^3$, $10^4$, $10^5$, $10^6$, $10^8$, $10^{12}$, or $10^{15}$ individual agents. A "population of agents" can be a library or a smaller population such as, a mixture less than 3, 5, 10, or 20 agents. A population of agents can be administered to the Aβ42/Tau transgenic fly and the flies can be screened for complete or partial reversion of a phenotype exhibited by the Aβ42/Tau transgenic fly. When a population of agents results in a change of the Aβ42/Tau transgenic fly phenotype, individual agents of the population can then be assayed independently to identify the particular agent of interest.

In a preferred embodiment, a high throughput screen of candidate agents is performed in which a large number of agents, at least 50 agents, 100 agents or more are tested individually in parallel on a plurality of fly populations. A fly population contains at least 2, 10, 20, 50, 100, or more adult flies or larvae. In one embodiment, locomotor phenotypes, behavioral phenotypes (e.g. appetite, mating behavior, and/or life span), or morphological phenotypes (e.g., shape size, or location of a cell, or organ, or appendage; or size shape, or growth rate of the fly) are observed by creating a digitized movie of the flies in the population and the movie is analyzed for fly phenotype.

B. Candidate Agents

Agents that are useful in the screening assays of the present inventions include biological or chemical compounds that when administered to a transgenic fly have the potential to modify an altered phenotype, e.g. partial or complete reversion of the phenotype. Agents include any recombinant, modified or natural nucleic acid molecule; library of recombinant, modified or natural nucleic acid molecules; synthetic, modified or natural peptides; library of synthetic, modified or natural peptides; organic or inorganic compounds; or library of organic or inorganic compounds, including small molecules. Agents can also be linked to a common or unique tag, which can facilitate recovery of the therapeutic agent.

Example agent sources include, but are not limited to, random peptide libraries as well as combinatorial chemistry-derived molecular library made of D- and/or L-configuration amino acids; phosphopeptides (including, but not limited to, members of random or partially degenerate, directed phosphopeptide libraries; see, e.g., Songyang et al., Cell 72:767-778 (1993)); antibodies (including, but not limited to, polyclonal, monoclonal, humanized, anti-idiotypic, chimeric or single chain antibodies, and FAb, F(ab')2 and FAb expression library fragments, and epitope-binding fragments thereof); and small organic or inorganic molecules.

Many libraries are known in the art that can be used, e.g. chemically synthesized libraries, recombinant libraries (e.g., produced by phage), and in vitro translation-based libraries. Examples of chemically synthesized libraries are described in Fodor et al., Science 251:767-773 (1991); Houghten et al., Nature 354:84-86 (1991); Lam et al., Nature 354:82-84 (1991); Medyuski, Bio/Technology 12:709-710 (1994); Gallop et al., J. Medicinal Chemistry 37(9):1233-1251 (1994); Ohlmeyer et al., Proc. Natl. Acad. Sci. USA 5 90: 10922-10926 (1993); Erb et al., Proc. Natl. Acad. Sci. USA 91:11422-11426 (1994); Houghten et al., Biotechniques 13:412 (1992); Jayawickreme et al., Proc. Natl. Acad. Sci. USA 91:1614-1618 (1994); Salmon et al., Proc. Natl. Acad. Sci. USA 90:11708-11712 (1993); PCT Publication No. WO 93/20242; and Brenner and Lerner, Proc. Natl. Acad. Sci. USA 89:5381-5383 (1992). By way of examples of nonpeptide libraries, a benzodiazopine library (see e.g., Bunin et al., Proc. Natl. Acad. Sci. USA 91:4708-4712 (1994)) can be adapted for use.

Peptoid libraries (Simon et al., Proc. Natl. Acad. Sci. USA 89:9367-9371 (1992)) can also be used. Another example of a library that can be used, in which the amide functionalities in peptides have been permethylated to generate a chemically transformed combinatorial library, is described by Ostreshet al. Proc. Natl. Acad. Sci. USA 91:11138-11142 (1994). Examples of phage display libraries wherein peptide libraries can be produced are described in Scott & Smith, Science 249:386-390 (1990); Devlin et al., Science, 249:404-406 (1990); Christian et al., J. Mol. Biol. 227:711-718 (1992); Lenska, J. Immunol. Meth. 152:149-157 (1992); Kay et al., Gene 128:59-65 (1993); and PCT Publication No. WO 94/18318 dated Aug. 18, 1994.

Agents that can be tested and identified by methods described herein can include, but are not limited to, compounds obtained from any commercial source, including Aldrich (Milwaukee, Wis. 53233), Sigma Chemical (St. Louis, Mo.), Fluka Chemie AG (Buchs, Switzerland) Fluka Chemical Corp. (Ronkonkoma, N.Y.); Eastman Chemical Company, Fine Chemicals (Kingsport, Tenn.), Boehringer Mannheim GmbH (Mannheim, 25 Germany), Takasago (Rockleigh, N.J.), SST Corporation (Clifton, N.J.), Ferro (Zachary, La. 70791), Riedel-deHaen Aktiengesellschaft (Seelze, Germany), PPG Industries Inc., Fine Chemicals (Pittsburgh, Pa. 15272). Further any kind of natural products may be screened using the methods described herein, including microbial, fungal, plant or animal extracts.

Furthermore, diversity libraries of test agents, including small molecule test compounds, may be utilized. For example, libraries may be commercially obtained from Specs and BioSpecs B.V. (Rijswijk, The Netherlands), Chembridge Corporation (San Diego, Calif.), Contract Service Company (Dolgoprudoy, Moscow Region, Russia), Comgenex USA Inc. (Princeton, N.J.), Maybridge Chemicals Ltd. (Cornwall PL34 0HW, United Kingdom), and Asinex (Moscow, Russia).

Still further, combinatorial library methods known in the art, can be utilized, including, but not limited to: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other approaches are applicable to peptide, non-peptide oligomer or small molecule libraries of compounds (Lam, Anticancer Drug Des. 12: 145 (1997)). Combinatorial libraries of test compounds, including small molecule test compounds, can be utilized, and may, for example, be generated as disclosed in Eichler & Houghten, Mol. Med. Today 1:174-180 (1995); Dolle, Mol. Divers. 2:223-236 (1997); and Lam, Anticancer Drug Des. 12:145-167 (1997).

Examples of methods for the synthesis of molecular libraries can be found in the art, for example in: DeWitt et al., Proc. Natl. Acad. Sci. USA 90:6909 (1993); Erb et al., Proc. Natl. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33:2059 (1994); Carell et al., Angew. Chem. Int. Ed. Engl. 33:2061 (1994); and Gallop et al., 15 J. Med. Chem. 37:1233 (1994).

A library of agents can also be a library of nucleic acid molecules; DNA, RNA, or analogs thereof. For example, a cDNA library can be constructed from mRNA collected from a cell, tissue, organ or organism of interest, or genomic DNA can be treated to produce appropriately sized fragments using restriction endonucleases or methods that randomly fragment genomic DNA. A library containing RNA molecules can be constructed, for example, by collecting RNA from cells or by synthesizing the RNA molecules chemically. Diverse libraries of nucleic acid molecules can be made using solid phase synthesis, which facilitates the production of randomized regions in the molecules. If desired, the randomization can be biased to produce a library of nucleic acid molecules containing particular percentages of one or more nucleotides at a position in the molecule (U.S. Pat. No. 5,270,163).

EXAMPLES

Example 1

Generation of a Aβ42/Tau Double Transgenic Fly

To generate an Aβ42/Tau double transgenic fly, a transgenic *Drosophila melanogaster* strain containing a transgene encoding Tau and a transgenic *Drosophila melanogaster* strain containing a transgene encoding human Aβ42 peptide were generated as described herein. The two transgenic fly strains were then crossed to obtain a double transgenic *Drosophila melanogaster* strain containing both Tau and human Aβ42 genes.

Transgene Constructs

The UAS/GAL4 system was used to generate both the Aβ42 and Tau transgenic flies. A cDNA encoding the longest human brain Tau isoform was cloned using standard ligation techniques (Sambrook et al., *Molecular Biology: A laboratory Approach*, Cold Spring Harbor, N.Y. 1989) into vector pUAST (Brand and Perrimon, Development 118:401-415 (1993)) as an EcoRI fragment in order to generate transformation vector, pUAS:$_{2N4R}$Tauwt. A schematic of the construct showing Tau inserted downstream of a UAS control element is depicted in FIG. 5a. The Tau isoform, which is represented by SEQ ID NO: 4 (nucleic acid sequence), and SEQ ID NO: 3 (amino acid sequence) contains Tau exons 2 and 3 as well as four microtubule-binding repeats.

Two pUAST transformation vectors carrying Aβ42 peptide were generated. One vector encodes Aβ42 peptide fused to the wingless (wg) signal peptide (pUAS:wg-Aβ42) and another vector encodes Aβ42 peptide fused to Argos (aos) signal peptide (pUAS:aos-Aβ42). To generate pUAS:wg-Aβ42, a DNA sequence encoding Aβ42 peptide (SEQ ID NO: 2) was first fused, in frame, to a synthetic oligonucleotide encoding the wingless (wg) signal peptide using a 4 amino acid linker (SFAM). The resulting DNA sequence that encodes the polypeptide MDISYIFVICLMALSGGSSFAM-DAEFRHDSGYEVHHQKLVFFAEDVGSNK-GAIIGLMVGGVVIA (SEQ ID NO: 16) was then cloned as an EcoRI fragment into vector pUAST (Brand and Perrimon, Development 118:401-415 (1993).

To generate pUAS:aos-Aβ42, the Argos (aos) signal peptide MPTTLMLLPCMLLLLLTAAAVAVGG (SEQ ID NO: 7) was PCR amplified from DNA encoding Argos and ligated in frame, to DNA encoding Aβ42 in the absence of a linker sequence. The DNA encoding Argos (aos) signal peptide fused in frame to Aβ42 was cloned into pUAST (Brand and Perrimon, Development 118:401-415 (1993)) as an EcoRI fragment (Schematic shown in FIG. 5a).

Transgenic Strains

To generate transgenic *Drosophila* lines expressing either Tau or Aβ42 the pUAST constructs described above, either pUAS:aos-Aβ42, or pUAS:$_{2N4R}$Tauwt were injected into a y$^1$w$^{118}$ *Drosophila Melanogaster* embryos as described in (Rubin and Spradling, Science 218:348-353, 1982).

In the case of pUAS:$_{2N4R}$Tauwt, 6 transgenic lines were generated and classified by visual inspection, as described herein, as strong (2 lines), medium (2 lines), and weak (2 lines) based on the severity of the eye phenotype observed after crossing with a gmr-GAL4 driver strain.

In the case of pUAS:aos-Aβ42-9 transgenic lines were generated and also classified as strong (2 lines), medium (2 lines), and weak (5 lines) based on the severity of the eye phenotype observed after crossing with a gmr-GAL4 driver strain. Transgenic *Drosophila* strains of moderate eye phenotype that carry the gmr-GAL4 driver and pUAS:aos-Aβ42 or pUAS:$_{2N4R}$Tauwt were then crossed to generate a double transgenic *Drosophila* line that express both Tau and human Aβ42 peptide. Crossing the single transgenic flies of moderate eye phenotype resulted in a synergistic eye phenotype classified as strong.

Figure 5B:
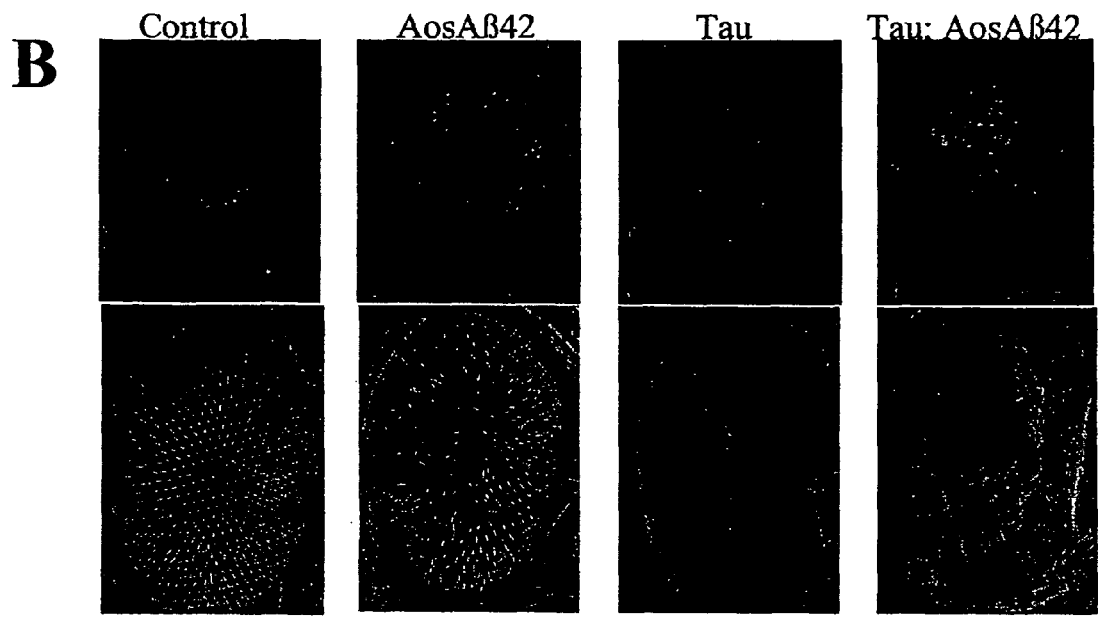
FIG. 5b shows eye phenotypes produced by Aβ42 and Tau in transgenic *Drosophila*.

FIG. 5b shows the synergistic rough eye phenotype of the double transgenic fly. Fresh eye (top row) and SEM images (bottom row) from 1-day-old flies carrying the gmr-GAL4 driver (control) and the aos-Aβ42, Tau, or aos-Aβ42 and Tau constructs are shown. Genotypes are as follows: yw; gmr-GAL4/+(column 1); yw; gmr-GAL4/+; UAS:AosAβ42 [M17A]/+(column 2); yw, gmr-GAL4, UAS:Tau[19y]/+(column 3); and yw; gmr-GAL4, UAS:Tau[19y]/+; UAS: AosAβ42[M17A]/+(column 4). All flies were developed at 27° C. When Aβ42 and Tau are coexpressed, the size of the eye is reduced to about one half of the control eye.

Figure 5C:
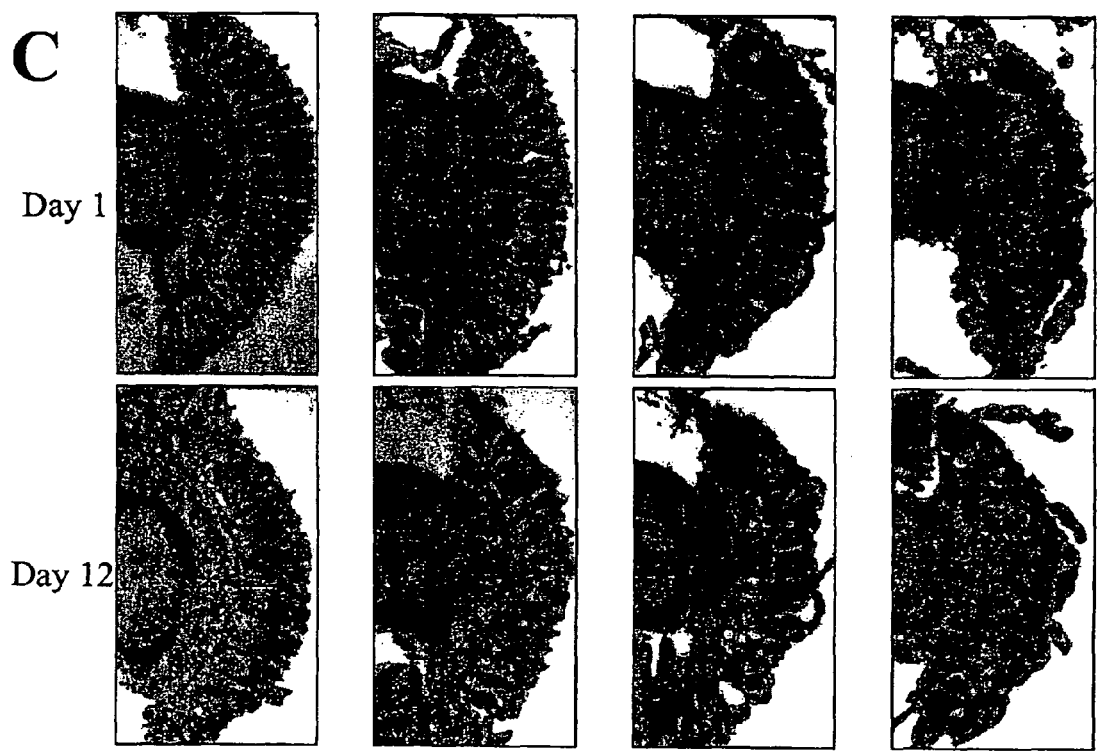
FIG. 5c shows that coexpression of Aβ42 and Tau enhances progressive retinal neurodegeneration.

FIG. 5c shows that coexpression of Aβ42 and Tau enhances progressive retinal degeneration. Eye sections were obtained from 1- and 12-day old flies carrying the gmr-GAL4 driver (control) and the constructs. There is normal thickness (arrow) of the retina in control flies at days 1 and 12. Expressing either Aβ42 or Tau leads to reduction in the thickness of the retina. In flies carrying both Aβ42 and Tau transgenes the retinal thickness phenotype is exacerbated. Note the proximity of the retina (arrow) and lamina (asterisk) in control flies.

In flies carrying either Tau or Aβ42, the retina and lamina are separated because the axonal layer connecting retinal neurons to the lamina (arrowhead) is enlarged and disorganized. This phenotype is most prominent in flies carrying both Tau and Aβ42. Comparing sections at day 1 and day 12 shows the progressivity of the retinal degeneration phenotypes: note increased vacuolization and further reduction of the retina at day 12. Genotypes in FIG. 5c are the same as in FIG. 5b.

In the case of transformation construct pUAS:wg-Aβ42, transgenic lines were generated by injecting the construct into a y$^1$w$^{118}$ *Drosophila Melanogaster* embryos as described in (Rubin and Spradling, Science 218:348-353, 1982) and screened for the insertion of transgene into genomic DNA by monitoring eye color. The pUAST vector carries the white gene marker. Transgenic *Drosophila* carrying wg-Aβ42 transgene were then crossed with elav-Gal4 driver strains for expression of the transgene in the central nervous system. The crosses did not result in a measurable phenotype, so the transgene was mobilized for expansion of copy number by crossing Transgenic *Drosophila* carrying wg-Aβ42 transgene with *Drosophila* that carry a source of P-element. Progeny from this cross were selected based on a change in eye color. Flies carrying higher copy numbers of wg-Aβ42 transgene were then crossed with elav-Gal4 driver strains and locomotor ability of the crossed flies was tested in climbing assays. Transgenic lines exhibited a locomotor phenotype and the flies were classified as strong (1 line), medium (2 lines), weak (9 lines) and very weak (28 lines) as compared among themselves and to elav-Gal4 driver control flies.

A double transgenic *Drosophila* carrying wg-Aβ42 and Tauwt transgenes was then generated by crossing a Tauwt transgenic *Drosophila* carrying an elav-Gal4 driver, with an wg-Aβ42 transgenic *Drosophila* carrying an elav-Gal4 driver. Locomotor ability was assessed and classified as strong (1 line), medium (2 lines), weak (9 lines) and very weak (28 lines) as compared to elav-Gal4 driver control flies.

Figure 6:
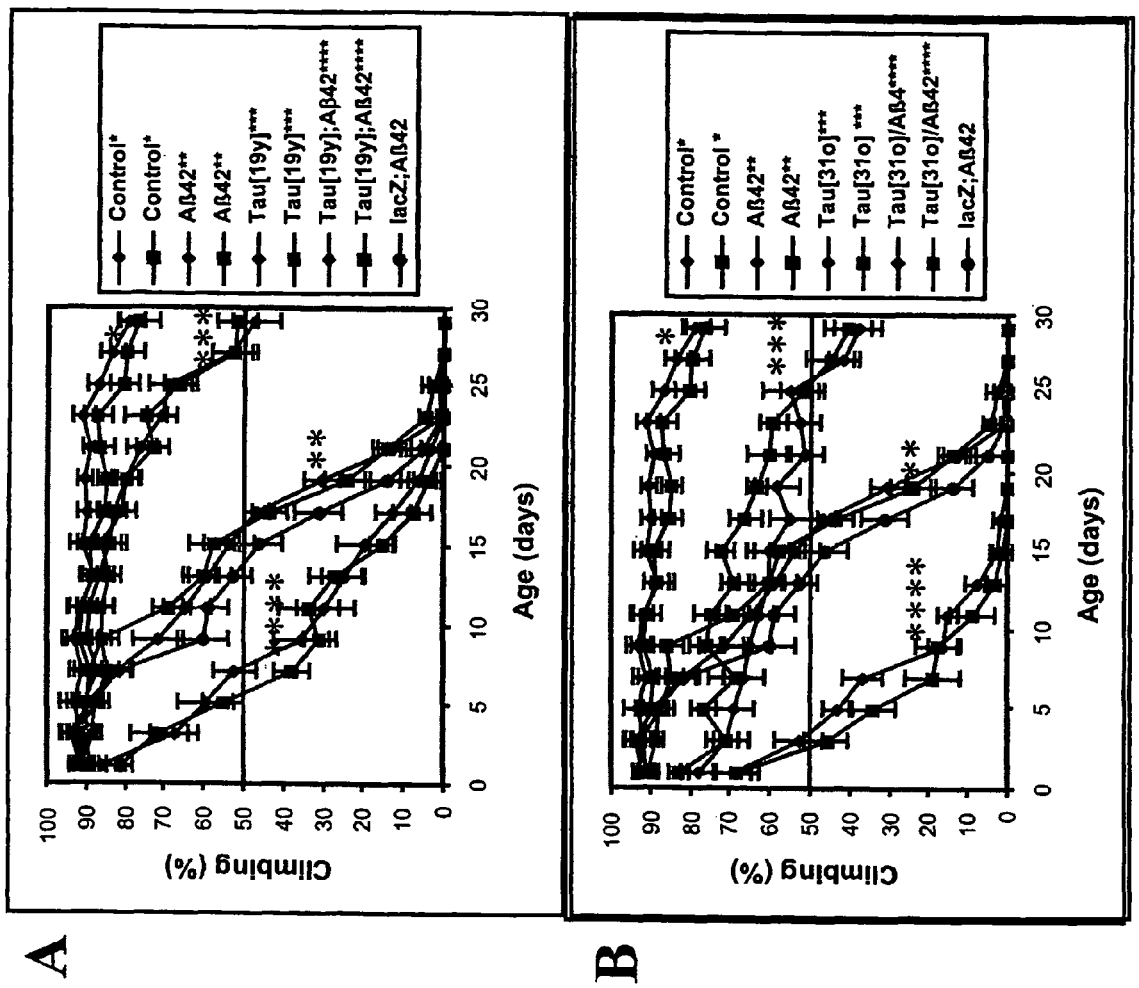
FIG. 6 shows synergistic interaction of Aβ42 and Tau in locomotor assays. Climbing assays were performed in duplicate for both medium (FIG. 6a) and strong (FIG. 6b) Tau lines.

FIG. 6 shows the synergistic interaction of Aβ42 and Tau in locomotor assays. Climbing performance as a function of age was determined for populations of flies of various genotypes at 27° C. Climbing assays were performed in duplicate (two groups of 30 individuals of the same age, ±4 hr; the sets are marked by *'s) and are presented for both medium (FIG. 6a) and strong (FIG. 6b) Tau lines. Genotypes are as follows: elav-GAL4/+(*set, control); elav-GAL4/+, UAS: Aosβ42[M17A]/+(set); elav-GAL4/+, UAS:Tau[19y]/+ (*set); elav-GAL4, UAS:Tau[19y]/+, UAS:Aosβ42 [M17A]/+(**set); elav-GAL4/+, UAS:Tau[31o]/+ (*set); elav-GAL4/+, UAS:Tau[31o]/UAS:Aosβ42 [M17A] (****set); elav-GAL4/+, UAS:lacZ/+, UAS: Aosβ42[M17A] (-o-). Bars show standard deviations.

*Drosophila* brain was then cyrosectioned, and horizontal cross sections of elav-GAL4; Tauwt/wg-Aβ42 flies were immunostained with anti-Tau conformation dependent antibodies ALZ50 and MCI. Positive staining of neurons was observed with both MCI antibody (data not shown) and ALZ50 antibody. The result shows that Tau protein, which is expressed in the brain of Aβ42/Tau double transgenic *Drosophila*, exhibits protein conformations associated with Alzheimer's disease.

Figure 7:
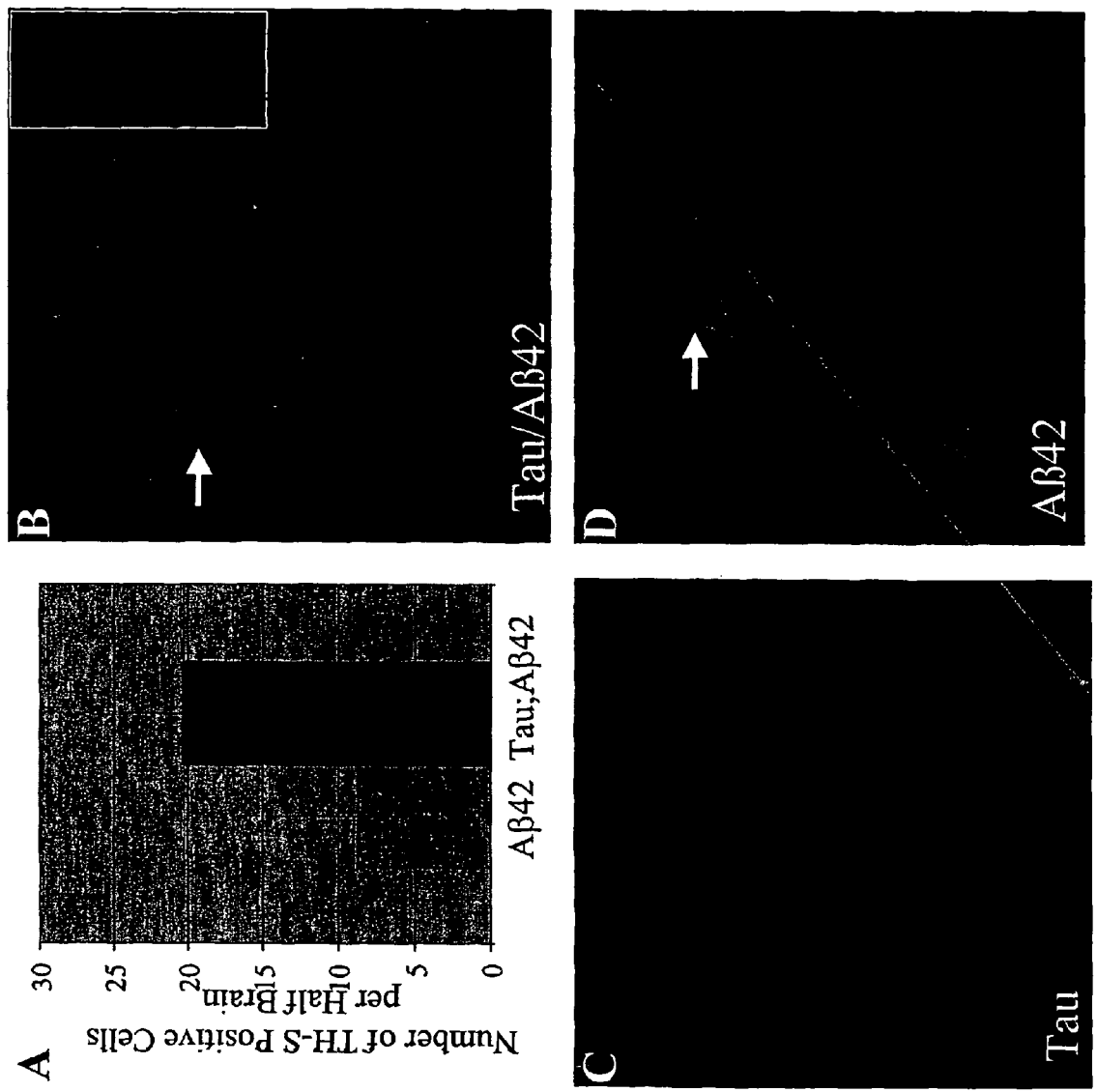
FIG. 7a is a graph representing the number of Thioflavin-S positive stained cells in flies expressing Aβ42 alone compared to flies expressing both Aβ42 and Tau.
FIG. 7b-d shows Thioflavin-S staining of cells and neurites in flies that express both Aβ42 and Tau (b), Tau alone (c), or Aβ42 alone (d).

Thioflavin-S staining was also performed on cells and neurites of the transgenic flies, described herein, to assess the presence of amyloid. Amyloids, when stained with Thioflavin-S, fluoresce an apple green color under a fluorescent microscope. The methods for Thioflavin-S staining are well known in the art. FIG. 7a shows the number of Thioflavin-S positive stained cells in flies expressing Aβ42 alone as compared to flies expressing both Aβ42 and Tau. FIG. 7b-c shows the Thioflavin-S staining observed by confocal imaging of the dorso-medial brain of 40-day old flies of the following genotypes: b), elav-GAL4/+, UAS:Aosβ42[M17A]/UAS:Tau[31o] b) elav-GAL4/+, UAS:Tau[31o]/+ and d) elav-Gal4/+, UAS:Aosβ42[M17A]/+. All flies were developed at 27° C. Thioflavin-S positive cells were not observed in flies expressing Tau only (FIG. 7c). Thioflavin-S positive cells were observed in flies expressing Aβ42 only (FIG. 7d). However, the number of Thioflavin-S-positive cells is much greater in flies expressing both Tau and Aβ42 (FIG. 7b). The insert in FIG. 7b shows a magnification of a Thioflavin-S-positive neurite. The number of Thioflavin-S-positive cells in flies expressing both Aβ42 and Tau is significantly greater than in flies carrying Aβ42 alone, p<0.001, (FIG. 7a, bars show standard deviations).

Example 2

Screening for a Therapeutic Agent

1. To screen for a therapeutic agent effective against Alzheimer's disease, candidate agents are administered to a plurality of the Aβ42$_{Iowa}$/Tau transgenic fly larvae that carry the gmr-GAL4 driver and the transgenes UAS:aos-Aβ42$_{Iowa}$ alone or in combination with UAS:$_{2N4R}$Tauwt. Candidate agents are microinjected into third instar transgenic Drosophila melanogaster larvae (three to 5 day old larvae). Larvae are injected through the cuticle into the hemolymph with defined amounts of each compound using a hypodermic needle of 20 gm internal diameter. Following injection, the larvae are placed into glass vials for completion of their development. After eclosion, the adult flies are anesthetized with $CO_2$ and visually inspected utilizing a dissecting microscope to assess for the reversion of the Drosophila eye phenotype as compared to control flies in which a candidate agent was not administered. An observed reversion of the Aβ42$_{Iowa}$/Tau transgenic fly eye phenotype towards the phenotype displayed by the control gmr-GAL4 driver strain is indicative of an agent that is useful for the treatment of Alzheimer's disease.

2. Screening for memory effect (Pavlovian Learning). Flies are trained by exposure to electroshock (12 pulses at 60 V, duration of 1.5 seconds, interval of 5 seconds) paired with one odor (benzaldehyde (BA, 4%) or methylcyclohexanol (MCH, 10°) for 60 seconds) and subsequent exposure to a second odor without electroshock. The odor concentrations are adjusted to assume no preference for flies exposed simultaneously to the two odors before the training. Immediately after training, learning is measured by allowing flies to choose between the two odors used during training. No preference between odors results in zero (no learning) performance index (PI). Avoidance of the odor previously paired with electroshock is expected to produce a $0<PI\leq1.00$ (see Tully, T. and Quinn, W. G., J. Comp. Physiol. A Sens. Neural. Behav. Physiol., 157:263-277 (1985)).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A transgenic *Drosophila* whose genome comprises a first DNA sequence that encodes a human amyloid β peptide Aβ42, and a second DNA sequence that encodes a human Tau protein, wherein each of said first and second DNA sequences is operatively linked to an expression control sequence, wherein said human Aβ42 and human Tau protein are coexpressed in a tissue of said transgenic *Drosophila*, and wherein said transgenic *Drosophila* exhibits an observable or measurable phenotype that is (i) changed compared to said phenotype in a control *Drosophila* or (ii) is absent from said control *Drosophila*, wherein said control *Drosophila* does not express said human Aβ42 and human Tau protein in said tissue.

2. The transgenic *Drosophila* of claim 1, wherein said expression control sequence is a tissue specific expression control sequence.

3. The transgenic *Drosophila* of claim 1, wherein said first DNA sequence is fused to a nucleic acid encoding a signal peptide.

4. A method for identifying a candidate agent for treating Alzheimer's disease, comprising the steps of:
 (a) providing a first transgenic *Drosophila* according to claim 1;
 (b) contacting said first transgenic *Drosophila* with an agent; and
 (c) observing or measuring an observable or measurable phenotype of said first transgenic *Drosophila* of step (b) and comparing it to said observable or measurable phenotype of a second *Drosophila* according to claim 1 not contacted with said candidate agent, wherein a difference in said observable or measurable phenotype of said first transgenic *Drosophila* compared to said second *Drosophila* is indicative of having identified a candidate agent for treating Alzheimer's disease.

5. The method of claim 4, wherein said transgenic *Drosophila* is an adult *Drosophila*.

6. The method of claim 4, wherein said transgenic *Drosophila* is in its larval stage.

7. The method of claim 4, wherein said expression control sequence is a tissue specific expression control sequence.

8. The method of claim 4, wherein said expression control sequence comprises a UAS control element.

9. The method of claim 4, wherein said first DNA sequence is fused to a nucleic acid encoding a signal peptide.

10. The method of claim 9, wherein said signal peptide is a wingless (wg) signal peptide.

11. The method of claim 9, wherein said signal peptide is a Argos (aos) signal peptide.

12. The method of claim 4, wherein said observable or measurable phenotype is selected from the group consisting of: rough eye phenotype; concave wing phenotype; behavioral phenotype; and locomotor dysfunction.

13. A method for identifying a candidate agent for treating Alzheimer's disease, comprising the steps of:
 (a) providing a transgenic *Drosophila* according to claim 1;
 (b) contacting said transgenic *Drosophila* with an agent; and
 (c) observing or measuring an observable or measurable phenotype of said transgenic *Drosophila* and comparing it to said observable or measurable phenotype of said *Drosophila* prior to contacting said *Drosophila* with said candidate agent, wherein a change in said phenotype after contacting with said candidate agent is indicative of having identified a candidate agent for treating Alzheimer's disease.

14. The method of claim 13, wherein said transgenic *Drosophila* is an adult *Drosophila*.

15. The method of claim 13, wherein said transgenic *Drosophila* is in its larval stage.

16. The method of claim 13, wherein said expression control sequence is a tissue specific expression control sequence.

17. The method of claim 13, wherein said expression control sequence comprises a UAS control element.

18. The method of claim 13, wherein said first DNA sequence is fused to a nucleic acid encoding a signal peptide.

19. The method of claim 18, wherein said signal peptide is a wingless (wg) signal peptide.

20. The method of claim 18, wherein said signal peptide is a Argos (aos) signal peptide.

21. The transgenic *Drosophila* of claim 1, wherein said observable or measurable phenotype is locomotor dysfunction or neural degeneration.

22. A transgenic *Drosophila* whose genome comprises a first DNA sequence that encodes a human amyloid β peptide Aβ42, and a second DNA sequence that encodes a human Tau protein, wherein each of said first and second DNA sequences is operatively linked to an expression control sequence, wherein said expression control sequence is elav, and wherein said transgenic *Drosophila* exhibits an altered phenotype selected from the group consisting of locomotor dysfunction and neural degeneration.

23. The method of claim 4, wherein said method includes, prior to said step of contacting, a step of obtaining said candidate agent.

24. The method of claim 13, wherein said method includes, prior to said step of contacting, a step of obtaining said candidate agent.

* * * * *

SEQUENCE LISTING

<160> NUMBER OF SEQ ID NOS: 16

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 129
<212> TYPE: DNA
<213> ORGANISM: Homo sapiens

<400> SEQUENCE: 2
gatgcagaat tccgacatga ctcaggatat gaagttcatc atcaaaaatt ggtgttcttt    60
gcagaagatg tgggttcaaa caaaggtgca atcattggac tcatggtggg cggtgttgtc    120
atagcgtga                                                            129

<210> SEQ ID NO 3
<211> LENGTH: 441

```
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400
```

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 4
<211> LENGTH: 1421
<212> TYPE: DNA
<213> ORGANISM: Homo sapiens

<400> SEQUENCE: 4

```
atggctgagc cccgccagga gttcgaagtg atggaagatc acgctgggac gtacgggttg    60
ggggacagga agatcagggg gggctacacc atgcaccaag accaagaggg tgacacggac   120
gctggcctga agaatctccc cctgcagacc cccactgagg acggatctga ggaaccgggc   180
tctgaaacct ctgatgctaa agcactcca acagcggaag atgtgacagc acccttagtg   240
gatgagggag ctcccggcaa gcaggctgcc gcgcagcccc acacggagat cccagaagga   300
accacagctg aagaagcagg cattggagac ccccagcc tggaagacga agctgctggt   360
cacgtgaccc aagctcgcat ggtcagtaaa agcaaagacg ggactggaag cgatgacaaa   420
aaagccaagg gggctgatgg taaaacgaag atcgccacac cgcggggagc agcccctcca   480
ggccagaagg ccaggccaa cgccaccagg attccagcaa aaaccccgcc cgctccaaag   540
acaccaccca gctctggtga acctccaaaa tcaggggatc gcagcggcta cagcagcccc   600
ggctccccag cactcccgg cagccgctcc cgcaccccgt cccttccaac cccacccacc   660
cgggagccca agaaggtggc agtggtccgt actccaccca gtcgccgtc ttccgccaag   720
agccgcctgc agacagcccc cgtgccatg ccagacctga gaatgtcaa gtccaagatc   780
ggctccactg agaacctgaa gcaccagccg ggaggcggga aggtgcagat aattaataag   840
aagctggatc ttagcaacgt ccagtccaag tgtggctcaa aggataatat caaacacgtc   900
ccgggaggcg gcagtgtgca aatagtctac aaaccagttg acctgagcaa ggtgacctcc   960
aagtgtggct cattaggcaa catccatcat aaaccaggag gtggccaggt ggaagtaaaa  1020
tctgagaagc ttgacttcaa ggacagagtc cagtcgaaga ttgggtccct ggacaatatc  1080
acccacgtcc ctggcggagg aaataaaaag attgaaaccc acaagctgac cttccgcgag  1140
aacgccaaag ccaagacaga ccacggggcg agatcgtgt acagtcgcc agtggtgtct  1200
ggggacacgt ctccacggca tctcagcaat gtctcctcca ccggcagcat cgacatggta  1260
gactcgcccc agctcgccac gctagctgac gaggtgtctg cctccctggc caagcagggt  1320
ttgtgatcag gccctgggg cggtcaataa ttgtggagag gagagaatga gagagtgtgg  1380
aaaaaaaag aataatgacc cggccccgc cctctgcccc c                       1421
```

<210> SEQ ID NO 5
<211> LENGTH: 18
<212> TYPE: PRT
<213> ORGANISM: Drosophila melanogaster

<400> SEQUENCE: 5

Met Asp Ile Ser Tyr Ile Phe Val Ile Cys Leu Met Ala Leu Ser Gly
1               5                   10                  15

Gly Ser

<210> SEQ ID NO 6
<211> LENGTH: 69
<212> TYPE: DNA
<213> ORGANISM: Drosophila melanogaster

<400> SEQUENCE: 6
atggatatca gctatatctt cgtcatctgc ctgatggccc tgtgcagcgg cggcagcagc    60
ttcgcgatg                                                            69

<210> SEQ ID NO 7
<211> LENGTH: 25
<212> TYPE: PRT
<213> ORGANISM: Drosophila melanogaster

<400> SEQUENCE: 7

Met Pro Thr Thr Leu Met Leu Leu Pro Cys Met Leu Leu Leu Leu
1               5                  10                  15

Thr Ala Ala Ala Val Ala Val Gly Gly
            20                  25

<210> SEQ ID NO 8
<211> LENGTH: 75
<212> TYPE: DNA
<213> ORGANISM: Drosophila melanogaster

<400> SEQUENCE: 8
atgcctacga cattgatgtt gctgccgtgc atgctgctgt tgctgctgac cgccgctgcc    60
gttgctgtcg gcggc                                                     75

<210> SEQ ID NO 9
<211> LENGTH: 27
<212> TYPE: PRT
<213> ORGANISM: Drosophila melanogaster

<400> SEQUENCE: 9

Met Cys Ala Ala Leu Arg Arg Asn Leu Leu Leu Arg Ser Leu Trp Val
1               5                  10                  15

Val Leu Ala Ile Gly Thr Ala Gln Val Gln Ala
            20                  25

<210> SEQ ID NO 10
<211> LENGTH: 20
<212> TYPE: PRT
<213> ORGANISM: Drosophila melanogaster

<400> SEQUENCE: 10

Met Ala Ala Val Asn Leu Gln Ala Ser Cys Ser Ser Gly Leu Ala Ser
1               5                  10                  15

Glu Asp Asp Ala
            20

<210> SEQ ID NO 11
<211> LENGTH: 23
<212> TYPE: PRT
<213> ORGANISM: Drosophila melanogaster

<400> SEQUENCE: 11

Met Met His Ile Leu Val Thr Leu Leu Leu Val Ala Ile His Ser Ile
1               5                  10                  15

Pro Thr Thr Trp Ala Val Thr
            20

<210> SEQ ID NO 12
<211> LENGTH: 3747
<212> TYPE: DNA
<213> ORGANISM: Homo sapiens

<400> SEQUENCE: 12

| | | | | | | |
|---|---|---|---|---|---|---|
| cctcccctgg | ggaggctcgc | gttcccgctg | ctcgcgcctg | ccgcccgccg | gcctcaggaa | 60 |
| cgcgccctct | cgccgcgcgc | gccctcgcag | tcaccgccac | ccaccagctc | cggcaccaac | 120 |
| agcagcgccg | ctgccaccgc | ccaccttctg | ccgccgccac | cacagccacc | ttctcctcct | 180 |
| ccgctgtcct | ctcccgtcct | cgcctctgtc | gactatcagg | tgaactttga | accaggatgg | 240 |
| ctgagcccg | ccaggagttc | gaagtgatgg | aagatcacgc | tgggacgtac | gggttggggg | 300 |
| acaggaaaga | tcagggggc | tacaccatgc | accaagacca | agagggtgac | acggacgctg | 360 |
| gcctgaaaga | atctcccctg | cagaccccca | ctgaggacgg | atctgaggaa | ccgggctctg | 420 |
| aaacctctga | tgctaagagc | actccaacag | cggaagatgt | gacagcaccc | ttagtggatg | 480 |
| agggagctcc | cggcaagcag | gctgccgcgc | agccccacac | ggagatccca | gaaggaacca | 540 |
| cagctgaaga | agcaggcatt | ggagacaccc | ccagcctgga | agacgaagct | gctggtcacg | 600 |
| tgacccaaga | gcctgaaagt | ggtaaggtgg | tccaggaagg | cttcctccga | gagccaggcc | 660 |
| ccccaggtct | gagccaccag | ctcatgtccg | gcatgcctgg | ggctcccctc | ctgcctgagg | 720 |
| gcccagaga | ggccacacgc | caaccttcgg | ggacaggacc | tgaggacaca | gagggcggcc | 780 |
| gccacgcccc | tgagctgctc | aagcaccagc | ttctaggaga | cctgcaccag | gaggggccgc | 840 |
| cgctgaaggg | ggcaggggc | aaagagaggc | cggggagcaa | ggaggaggtg | gatgaagacc | 900 |
| gcgacgtcga | tgagtcctcc | ccccaagact | ccctccctc | caaggcctcc | ccagcccaag | 960 |
| atgggcggcc | tccccagaca | gccgccagag | aagccaccag | catcccaggc | ttcccagcgg | 1020 |
| agggtgccat | cccctccct | gtggatttcc | tctccaaagt | ttccacagag | atcccagcct | 1080 |
| cagagcccga | cgggcccagt | gtagggcggg | ccaaagggca | ggatgccccc | ctggagttca | 1140 |
| cgtttcacgt | ggaaatcaca | cccaacgtgc | agaaggagca | ggcgcactcg | gaggagcatt | 1200 |
| tgggaagggc | tgcatttcca | ggggcccctg | agagggggcc | agaggcccgg | gcccctctt | 1260 |
| tgggagagga | cacaaaagag | gctgaccttc | cagagccctc | tgaaaagcag | cctgctgctg | 1320 |
| ctccgcgggg | gaagcccgtc | agccgggtcc | ctcaactcaa | agctcgcatg | gtcagtaaaa | 1380 |
| gcaaagacgg | gactggaagc | gatgacaaaa | aagccaagac | atccacacgt | tcctctgcta | 1440 |
| aaaccttgaa | aaataggcct | tgccttagcc | ccaaactccc | cactcctggt | agctcagacc | 1500 |
| ctctgatcca | accctccagc | cctgctgtgt | gcccagagcc | accttcctct | cctaaacacg | 1560 |
| tctcttctgt | cacttcccga | actggcagtt | ctggagcaaa | ggagatgaaa | ctcaagggg | 1620 |
| ctgatggtaa | aacgaagatc | gccacaccgc | ggggagcagc | cctccaggc | cagaagggcc | 1680 |
| aggccaacgc | caccaggatt | ccagcaaaaa | ccccgcccgc | tccaaagaca | ccacccagct | 1740 |
| ctggtgaacc | tccaaaatca | ggggatcgca | gcggctacag | cagcccggc | tcccaggca | 1800 |
| ctcccggcag | ccgctcccgc | accccgtccc | ttcaacccc | acccacccgg | gagcccaaga | 1860 |
| aggtggcagt | ggtccgtact | ccacccaagt | cgccgtcttc | cgccaagagc | cgcctgcaga | 1920 |
| cagcccccgt | gcccatgcca | gacctgaaga | atgtcaagtc | caagatcggc | tccactgaga | 1980 |
| acctgaagca | ccagccggga | ggcgggaagg | tgcagataat | taataagaag | ctggatctta | 2040 |
| gcaacgtcca | gtccaagtgt | ggctcaaagg | ataatatcaa | acacgtcccg | ggaggcggca | 2100 |

-continued

```
gtgtgcaaat agtctacaaa ccagttgacc tgagcaaggt gacctccaag tgtggctcat    2160
taggcaacat ccatcataaa ccaggaggtg gccaggtgga agtaaaatct gagaagcttg    2220
acttcaagga cagagtccag tcgaagattg ggtccctgga caatatcacc cacgtccctg    2280
gcggaggaaa taaaaagatt gaaacccaca agctgacctt ccgcgagaac gccaaagcca    2340
agacagacca cggggcggag atcgtgtaca agtcgccagt ggtgtctggg gacacgtctc    2400
cacggcatct cagcaatgtc tcctccaccg gcagcatcga catggtagac tcgccccagc    2460
tcgccacgct agctgacgag gtgtctgcct ccctggccaa gcagggtttg tgatcaggcc    2520
cctggggcgg tcaataattg tggagaggag agaatgagag agtgtggaaa aaaaaagaat    2580
aatgacccgg cccccgccct ctgccccag ctgctcctcg cagttcggtt aattggttaa    2640
tcacttaacc tgcttttgtc actcggcttt ggctcggac ttcaaaatca gtgatgggag    2700
taagagcaaa tttcatcttt ccaaattgat gggtgggcta gtaataaaat atttaaaaaa    2760
aaacattcaa aaacatggcc acatccaaca tttcctcagg caattccttt tgattctttt    2820
ttcttccccc tccatgtaga agagggagaa ggagaggctc tgaaagctgc ttctggggga    2880
tttcaaggga ctgggggtgc caaccacctc tggccctgtt gtgggggttg tcacagaggc    2940
agtggcagca acaaaggatt tgaaaacttt ggtgtgttcg tggagccaca ggcagacgat    3000
gtcaaccttg tgtgagtgtg acggggggttg gggtggggcg ggaggccacg ggggaggccg    3060
aggcaggggc tgggcagagg ggaggaggaa gcacaagaag tgggagtggg agaggaagcc    3120
acgtgctgga gagtagacat ccccctcctt gccgctggga gagccaaggc ctatgccacc    3180
tgcagcgtct gagcggccgc ctgtccttgg tggccggggg tggggccctg ctgtgggtca    3240
gtgtgccacc ctctgcaggg cagcctgtgg gagaagggac agcgggttaa aaagagaagg    3300
caagcctggc aggagggttg gcacttcgat gatgacctcc ttagaaagac tgaccttgat    3360
gtcttgagag cgctggcctc ttcctccctc cctgcagggt agggcgcctg agcctaggcg    3420
gttccctctg ctccacagaa accctgtttt attgagttct gaaggttgga actgctgcca    3480
tgattttggc cactttgcag acctgggact ttagggctaa ccagttctct ttgtaaggac    3540
ttgtgcctct tgggagacgt ccacccgttt ccaagcctgg gccactggca tctctggagt    3600
gtgtgggggt ctgggaggca ggtcccgagc cccctgtcct tcccacggcc actgcagtca    3660
ccccgtctgc gccgctgtgc tgttgtctgc cgtgagagcc caatcactgc ctatacccct    3720
catcacacgt cacaatgtcc cgaattc                                       3747
```

<210> SEQ ID NO 13
<211> LENGTH: 2796
<212> TYPE: DNA
<213> ORGANISM: Homo sapiens

<400> SEQUENCE: 13

```
cctcccctgg ggaggctcgc gttcccgctg ctcgcgcctg ccgcccgccg gcctcaggaa      60
cgcgccctct cgccgcgcgc gccctcgcag tcaccgccac ccaccagctc cggcaccaac     120
agcagcgccg ctgccaccgc ccaccttctg ccgccgccac cacagccacc ttctcctcct     180
ccgctgtcct ctcccgtcct cgcctctgtc gactatcagg tgaactttga accaggatgg     240
ctgagccccg ccaggagttc gaagtgatgg aagatcacgc tggacgtac gggttggggg     300 acaggaaaga tcagggggc tacaccatgc accaagacca agagggtgac acggacgctg     360
gcctgaaaga atctccctg cagaccccca ctgaggacgg atctgaggaa ccgggctctg     420
aaacctctga tgctaagagc actccaacag cggaagatgt gacagcaccc ttagtggatg     480
```

-continued

```
agggagctcc cggcaagcag gctgccgcgc agccccacac ggagatccca gaaggaacca      540
cagctgaaga agcaggcatt ggagacaccc ccagcctgga agacgaagct gctggtcacg      600
tgacccaagc tcgcatggtc agtaaaagca agacgggac tggaagcgat gacaaaaaag       660 ccaaggggc tgatggtaaa cgaagatcg ccacaccgcg gggagcagcc cctccaggcc        720
agaagggcca ggccaacgcc accaggattc cagcaaaaac cccgcccgct ccaaagacac      780
cacccagctc tggtgaacct ccaaaatcag gggatcgcag cggctacagc agccccggct     840
ccccaggcac tcccggcagc cgctcccgca ccccgtccct tccaaccccca cccacccggg    900 agcccaagaa ggtggcagtg gtccgtactc cacccaagtc gccgtcttcc gccaagagcc     960
gcctgcagac agcccccgtg cccatgccag acctgaagaa tgtcaagtcc aagatcggct    1020
ccactgagaa cctgaagcac cagccgggag gcggaaggt gcagataatt aataagaagc     1080
tggatcttag caacgtccag tccaagtgtg gctcaaagga taatatcaaa cacgtcccgg    1140
gaggcggcag tgtgcaaata gtctacaaac cagttgacct gagcaaggtg acctccaagt    1200
gtggctcatt aggcaacatc catcataaac caggaggtgg ccaggtggaa gtaaaatctg    1260
agaagcttga cttcaaggac agagtccagt cgaagattgg gtccctggac aatatcaccc    1320
acgtccctgg cggaggaaat aaaaagattg aaacccacaa gctgaccttc cgcgagaacg    1380
ccaaagccaa gacagaccac ggggcggaga tcgtgtacaa gtcgccagtg gtgtctgggg    1440
acacgtctcc acggcatctc agcaatgtct cctccaccgg cagcatcgac atggtagact    1500
cgccccagct cgccacgcta gctgacgagg tgtctgcctc cctggccaag cagggtttgt    1560
gatcaggccc ctggggcggt caataattgt ggagaggaga gaatgagaga gtgtggaaaa    1620
aaaaagaata atgaccccgg ccccgccctc tgccccagc tgctcctcgc agttcggtta     1680
attggttaat cacttaacct gcttttgtca ctcggctttg gctcgggact tcaaaatcag    1740
tgatgggagt aagagcaaat ttcatctttc caaattgatg ggtgggctag taataaaata    1800
tttaaaaaaa aacattcaaa aacatggcca catccaacat ttcctcaggc aattccttt     1860 gattctttt tcttcccccct ccatgtagaa gagggagaag gagaggctct gaaagctgct   1920
tctgggggat ttcaagggac tggggggtgcc aaccacctct ggccctgttg tgggggttgt   1980
cacagaggca gtggcagcaa caaaggattt gaaaactttg gtgtgttcgt ggagccacag    2040
gcagacgatg tcaaccttgt gtgagtgtga cggggggttgg ggtggggcgg gaggccacgg   2100
gggaggccga ggcagggggct gggcagaggg gaggaggaag cacaagaagt gggagtggga    2160
gaggaagcca cgtgctggag agtagacatc ccctccttg ccgctgggag agccaaggcc     2220
tatgccacct gcagcgtctg agcggccgcc tgtccttggt ggccggggt ggggcctgc     2280 tgtgggtcag tgtgccaccc tctgcagggc agcctgtggg agaagggaca gcgggttaaa    2340
aagagaaggc aagcctggca ggagggttgg cacttcgatg atgacctcct tagaaagact    2400
gaccttgatg tcttgagagc gctggcctct tcctccctcc ctgcagggta gggcgcctga    2460
gcctaggcgg ttccctctgc tccacagaaa ccctgttttta ttgagttctg aaggttgaa    2520 ctgctgccat gatttttggcc actttgcaga cctgggactt tagggctaac cagttctctt    2580
```

-continued

| | |
|---|---|
| tgtaaggact tgtgcctctt gggagacgtc cacccgtttc caagcctggg ccactggcat | 2640 |
| ctctggagtg tgtggggtc tgggaggcag gtcccgagcc ccctgtcctt cccacggcca | 2700 |
| ctgcagtcac cccgtctgcg ccgctgtgct gttgtctgcc gtgagagccc aatcactgcc | 2760 |
| tataccoctc atcacacgtc acaatgtccc gaattc | 2796 |

<210> SEQ ID NO 14
<211> LENGTH: 2622
<212> TYPE: DNA
<213> ORGANISM: Homo sapiens

<400> SEQUENCE: 14

| | |
|---|---|
| cctcccctgg ggaggctcgc gttcccgctg ctcgcgcctg ccgcccgccg gcctcaggaa | 60 |
| cgcgccctct cgccgcgcgc gccctcgcag tcaccgccac ccaccagctc cggcaccaac | 120 |
| agcagcgccg ctgccaccgc ccaccttctg ccgccgccac cacagccacc ttctcctcct | 180 |
| ccgctgtcct ctcccgtcct cgcctctgtc gactatcagg tgaactttga accaggatgg | 240 |
| ctgagccccg ccaggagttc gaagtgatgg aagatcacgc tgggacgtac gggttggggg | 300 |
| acaggaaaga tcaggggggc tacaccatgc accaagacca agaggtgac acggacgctg | 360 |
| gcctgaaagc tgaagaagca ggcattggag acaccccag cctggaagac gaagctgctg | 420 |
| gtcacgtgac ccaagctcgc atggtcagta aagcaaaga cgggactgga agcgatgaca | 480 |
| aaaaagccaa gggggctgat ggtaaaacga agatcgccac accgcgggga gcagcccctc | 540 |
| caggccagaa gggccaggcc aacgccacca ggattccagc aaaaacccg cccgctccaa | 600 |
| agacaccacc cagctctggt gaacctccaa aatcagggga tcgcagcggc tacagcagcc | 660 |
| ccggctcccc aggcactccc ggcagccgct cccgcacccc gtcccttcca acccacccca | 720 |
| cccgggagcc caagaaggtg cagtggtcc gtactccacc caagtcgccg tcttccgcca | 780 |
| agagccgcct gcagacagcc cccgtgccca tgccagacct gaagaatgtc aagtccaaga | 840 |
| tcggctccac tgagaacctg aagcaccagc cgggaggcgg gaaggtgcag ataattaata | 900 |
| agaagctgga tcttagcaac gtccagtcca agtgtggctc aaaggataat atcaaacacg | 960 |
| tcccgggagg cggcagtgtg caaatagtct acaaaccagt tgacctgagc aaggtgacct | 1020 |
| ccaagtgtgg ctcattaggc aacatccatc ataaaccagg aggtggccag gtggaagtaa | 1080 |
| aatctgagaa gcttgacttc aaggacagag tccagtcgaa gattgggtcc ctggacaata | 1140 |
| tcacccacgt ccctggcgga ggaaataaaa agattgaaac ccacaagctg accttccgcg | 1200 |
| agaacgccaa agccaagaca gaccacgggg cggagatcgt gtacaagtcg ccagtggtgt | 1260 |
| ctggggacac gtctccacgg catctccagca atgtctcctc caccggcagc atcgacatgg | 1320 |
| tagactcgcc ccagctcgcc acgctagctg acgaggtgtc tgcctccctg gccaagcagg | 1380 |
| gtttgtgatc aggcccctgg ggcggtcaat aattgtggag aggagagaat gagagagtgt | 1440 |
| ggaaaaaaaa agaataatga cccggccccc gccctctgcc cccagctgct cctcgcagtt | 1500 |
| cggttaattg gttaatcact taacctgctt ttgtcactcg gctttggctc gggacttcaa | 1560 |
| aatcagtgat gggagtaaga gcaaatttca tctttccaaa ttgatgggtg gctagtaat | 1620 |
| aaaatattta aaaaaaaaca ttcaaaaaca tggccacatc caacatttcc tcaggcaatt | 1680 |
| ccttttgatt cttttttctt cccctccat gtagaagagg gagaaggaga ggctctgaaa | 1740 |
| gctgcttctg ggggatttca agggactggg ggtgccaacc acctctggcc ctgttgtggg | 1800 |
| ggttgtcaca gaggcagtgg cagcaacaaa ggatttgaaa actttggtgt gttcgtggag | 1860 |
| ccacaggcag acgatgtcaa ccttgtgtga gtgtgacggg ggttggggtg gggcgggagg | 1920 |

| | |
|---|---|
| ccacggggga ggccgaggca ggggctgggc agaggggagg aggaagcaca agaagtggga | 1980 |
| gtgggagagg aagccacgtg ctggagagta gacatccccc tccttgccgc tgggagagcc | 2040 |
| aaggcctatg ccacctgcag cgtctgagcg gccgcctgtc cttggtggcc gggggtgggg | 2100 |
| gcctgctgtg ggtcagtgtg ccaccctctg cagggcagcc tgtgggagaa gggacagcgg | 2160 |
| gttaaaaaga gaaggcaagc ctggcaggag ggttggcact tcgatgatga cctccttaga | 2220 |
| aagactgacc ttgatgtctt gagagcgctg gcctcttcct ccctccctgc agggtagggc | 2280 |
| gcctgagcct aggcggttcc ctctgctcca cagaaaccct gttttattga gttctgaagg | 2340 |
| ttggaactgc tgccatgatt ttggccactt tgcagacctg ggactttagg gctaaccagt | 2400 |
| tctctttgta aggacttgtg cctcttggga gacgtccacc cgtttccaag cctgggccac | 2460 |
| tggcatctct ggagtgtgtg ggggtctggg aggcaggtcc cgagccccct gtccttccca | 2520 |
| cggccactgc agtcaccccg tctgcgccgc tgtgctgttg tctgccgtga gagcccaatc | 2580 |
| actgcctata cccctcatca cacgtcacaa tgtcccgaat tc | 2622 |

<210> SEQ ID NO 15
<211> LENGTH: 2529
<212> TYPE: DNA
<213> ORGANISM: Homo sapiens

<400> SEQUENCE: 15

| | |
|---|---|
| cctcccctgg ggaggctcgc gttcccgctg ctcgcgcctg ccgccgccg gcctcaggaa | 60 |
| cgcgccctct cgccgcgcgc gccctcgcag tcaccgccac ccaccagctc cggcaccaac | 120 |
| agcagcgccg ctgccaccgc ccaccttctg ccgccgccac cacagccacc ttctcctcct | 180 |
| ccgctgtcct ctcccgtcct cgcctctgtc gactatcagg tgaactttga accaggatgg | 240 |
| ctgagccccg ccaggagttc gaagtgatgg aagatcacgc tgggacgtac gggttggggg | 300 |
| acaggaaaga tcaggggggc tacaccatgc accaagacca agagggtgac acggacgctg | 360 |
| gcctgaaagc tgaagaagca ggcattggag acaccccag cctggaagac gaagctgctg | 420 |
| gtcacgtgac ccaagctcgc atggtcagta aaagcaaaga cgggactgga agcgatgaca | 480 |
| aaaaagccaa gggggctgat ggtaaaacga agatcgccac accgcgggga gcagcccctc | 540 |
| caggccagaa gggccaggcc aacgccacca ggattccagc aaaaacccg cccgctccaa | 600 |
| agacaccacc cagctctggt gaacctccaa atcagggga tcgcagcggc tacagcagcc | 660 |
| ccggctcccc aggcactccc ggcagccgct cccgcacccc gtcccttcca accccaccca | 720 |
| cccgggagcc caagaaggtg gcagtggtcc gtactccacc caagtcgccg tcttccgcca | 780 |
| agagccgcct gcagacagcc cccgtgccca tgccagacct gaagaatgtc aagtccaaga | 840 |
| tcggctccac tgagaacctg aagcaccagc cggaggcgg gaaggtgcaa atagtctaca | 900 |
| aaccagttga cctgagcaag gtgacctcca agtgtggctc attaggcaac atccatcata | 960 |
| aaccaggagg tggccaggtg gaagtaaaat ctgagaagct tgacttcaag gacagagtcc | 1020 |
| agtcgaagat tgggtccctg gacaatatca cccacgtccc tggcggagga aataaaaaga | 1080 |
| ttgaaaccca caagctgacc ttccgcgaga acgccaaagc caagacagac cacggggcgg | 1140 |
| agatcgtgta caagtcgcca gtggtgtctg gggacacgtc tccacggcat ctcagcaatg | 1200 |

```
tctcctccac cggcagcatc gacatggtag actcgcccca gctcgccacg ctagctgacg   1260
aggtgtctgc ctccctggcc aagcagggtt tgtgatcagg ccctgggggc ggtcaataat   1320
tgtggagagg agagaatgag agagtgtgga aaaaaaaaga ataatgaccc ggcccccgcc   1380
ctctgccccc agctgctcct cgcagttcgg ttaattggtt aatcacttaa cctgcttttg   1440
tcactcggct ttggctcggg acttcaaaat cagtgatggg agtaagagca aatttcatct   1500
ttccaaattg atgggtgggc tagtaataaa atatttaaaa aaaaacattc aaaaacatgg   1560
ccacatccaa catttcctca ggcaattcct tttgattctt ttttcttccc cctccatgta   1620
gaagagggag aaggagaggc tctgaaagct gcttctgggg gatttcaagg gactgggggt   1680
gccaaccacc tctggccctg ttgtgggggt tgtcacagag gcagtggcag caacaaagga   1740
tttgaaaact ttggtgtgtt cgtggagcca caggcagacg atgtcaacct tgtgtgagtg   1800 tgacggggt tggggtgggg cgggaggcca cggggaggc cgaggcaggg gctgggcaga    1860
ggggaggagg aagcacaaga agtgggagtg ggagaggaag ccacgtgctg gagagtagac   1920 atcccctcc ttgccgctgg gagagccaag gcctatgcca cctgcagcgt ctgagcggcc   1980
gcctgtcctt ggtggccggg ggtgggggcc tgctgtgggt cagtgtgcca ccctctgcag   2040
ggcagcctgt gggagaaggg acagcgggtt aaaagagaa ggcaagcctg caggagggt    2100 tggcacttcg atgatgacct ccttagaaag actgaccttg atgtcttgag agcgctggcc   2160
tcttcctccc tccctgcagg gtagggcgcc tgagcctagg cggttccctc tgctccacag   2220
aaaccctgtt ttattgagtt ctgaaggttg gaactgctgc catgattttg gccactttgc   2280
agacctggga ctttagggct aaccagttct ctttgtaagg acttgtgcct cttgggagac   2340
gtccacccgt ttccaagcct gggccactgg catctctgga gtgtgtgggg gtctgggagg   2400
caggtcccga gcccctgtc cttcccacgg ccactgcagt caccccgtct gcgccgctgt   2460
gctgttgtct gccgtgagag cccaatcact gcctataccc ctcatcacac gtcacaatgt   2520
cccgaattc                                                          2529
```

<210> SEQ ID NO 16
<211> LENGTH: 64
<212> TYPE: PRT
<213> ORGANISM: Artificial
<220> FEATURE:
<223> OTHER INFORMATION: Synthetic wg-AB42 Fusion Peptide

<400> SEQUENCE: 16

```
Met Asp Ile Ser Tyr Ile Phe Val Ile Cys Leu Met Ala Leu Ser Gly
1               5                   10                  15

Gly Ser Ser Phe Ala Met Asp Ala Glu Phe Arg His Asp Ser Gly Tyr
            20                  25                  30

Glu Val His His Gln Lys Leu Val Phe Phe Ala Glu Asp Val Gly Ser
        35                  40                  45

Asn Lys Gly Ala Ile Ile Gly Leu Met Val Gly Gly Val Val Ile Ala
    50                  55                  60
```